United States Patent [19]
Gaukel

[11] Patent Number: 6,072,396
[45] Date of Patent: Jun. 6, 2000

[54] APPARATUS AND METHOD FOR CONTINUOUS ELECTRONIC MONITORING AND TRACKING OF INDIVIDUALS

[75] Inventor: John J. Gaukel, Omaha, Nebr.

[73] Assignee: Advanced Business Sciences, Omaha, Nebr.

[21] Appl. No.: 08/840,057

[22] Filed: Apr. 24, 1997

Related U.S. Application Data

[63] Continuation-in-part of application No. 08/367,057, Dec. 30, 1994.

[51] Int. Cl.[7] .................................................. G08B 21/00
[52] U.S. Cl. .................. 340/573.4; 340/539; 340/693.5; 340/825.32; 340/825.49; 342/357; 364/449.6; 379/38
[58] Field of Search ................................ 340/573.4, 539, 340/693.5, 825.3, 825.31, 825.32, 825.49, 825.54; 342/357; 364/449.6; 379/38

[56] References Cited

U.S. PATENT DOCUMENTS

| | | | |
|---|---|---|---|
| 4,319,241 | 3/1982 | Mount | 340/870.38 |
| 4,673,936 | 6/1987 | Kotoh | 342/51 |
| 4,741,245 | 5/1988 | Malone | 89/41.03 |
| 4,819,053 | 4/1989 | Halavais | 342/353 |
| 4,885,571 | 12/1989 | Pauley et al. | 340/573.4 |
| 5,019,828 | 5/1991 | Schoolman | 342/457 |
| 5,043,736 | 8/1991 | Darnell et al. | 342/357 |
| 5,146,231 | 9/1992 | Ghaem et al. | 342/419 |
| 5,198,831 | 3/1993 | Burrell et al. | 343/895 |
| 5,317,309 | 5/1994 | Vercellotti et al. | 340/825.54 |
| 5,334,974 | 8/1994 | Simms et al. | 340/990 |
| 5,416,468 | 5/1995 | Baumann | 340/573.1 |
| 5,416,695 | 5/1995 | Stutman et al. | 600/300 |
| 5,437,278 | 8/1995 | Wilk | 600/425 |
| 5,461,365 | 10/1995 | Schlager et al. | 340/573.4 |
| 5,461,390 | 10/1995 | Hoshen | 342/419 |
| 5,493,694 | 2/1996 | Vlcek et al. | 455/52.1 |
| 5,497,149 | 3/1996 | Fast | 340/988 |
| 5,528,248 | 6/1996 | Steiner et al. | 342/357 |
| 5,541,845 | 7/1996 | Klein | 701/207 |
| 5,544,661 | 8/1996 | Davis et al. | 128/904 |
| 5,552,772 | 9/1996 | Janky et al. | 340/573.4 |
| 5,559,497 | 9/1996 | Hong | 340/573.1 |
| 5,568,119 | 10/1996 | Schipper et al. | 340/825.37 |
| 5,652,570 | 7/1997 | Lepkofker | 340/573.4 |
| 5,731,757 | 3/1998 | Layson, Jr. | 340/573 |

*Primary Examiner*—Glen Swann
*Attorney, Agent, or Firm*—Zarley, McKee, Thomte Voorhees & Sease; Dennis L. Thomte

[57] ABSTRACT

An apparatus and method of monitoring mobile objects or persons using the utilizes the Global Positioning System satellites and cellular telephone communications. The apparatus may include first and second remote units adapted to be worn on the monitored person or object. These remote units would comprise the position and data sensors as well as the transmitter device to transmit the information back to a central tracking station. The remote units may be operative to monitor many data items such as system integrity, motion temperature, audio, and the like in addition to position. This data would then be transmitted back to a central monitoring station operative to process and display the information. The system is also adapted to monitor persons in hazardous environments such as radioactivity or poisonous gases or even to monitor inanimate objects such as automobiles.

41 Claims, 15 Drawing Sheets

APPARATUS AND METHOD FOR CONTINUOUS ELECTRONIC MONITORING AND TRACKING OF INDIVIDUALS

CROSS-REFERENCE TO RELATED APPLICATION

This is a continuation-in-part application of Ser. No. 08/367,057 filed Dec. 30, 1994.

TECHNICAL FIELD

The apparatus and method of the present invention relate generally to position monitoring. More specifically, the invention relates to a method and apparatus for tracking the position of an individual, monitoring selected bits of data regarding that person, and for real time notification of non-compliance with predetermined parameters.

BACKGROUND OF THE INVENTION

The present invention has great utility in many varied settings. For example, the apparatus may be used in the "house arrest" or "home parole" setting. In that case, it is critical that the person remain at home or within prescribed geographical limits. Alternatively, the whereabouts or medical condition of elderly or infirm persons might be monitored. The present invention provides such a device which is capable of monitoring position as well as certain health related parameters such as heart rate, blood pressure or the like. The present invention is not however limited to the monitoring of individuals, rather it is applicable to monitoring any mobile object. For example, the present invention can be used to detect and track stolen cars.

The term "environmental information" will be used herein to refer to information which may be gleaned from the person or object wearing the device, or his/its surroundings. Examples of such environmental data may be, but are not limited to, sound, temperature, motion, and the like.

There is a current move in our nation to stem the growth in the crime rate by building more prisons and hence incarcerating more people. Part of this stems from pressure from the public to keep hard core or habitual criminals locked up for the full length of their sentence. This pressure is balanced against an even stronger push by the public to keep cost of government down.

One recent solution to this dilemma has been "house arrest" technology, which allows minor offense sentences to be carried out in the home. The system consists of a transponder which the convicted person must wear, which must be present when that person is called by the police to verify presence at home or work. One severe drawback of this process involves use of man-hours and the associated cost of doing on-site inspections to ensure that the monitored persons are actually where they say they are. Additionally, there are several ways to fool the system if this manual checking is not implemented. Consequently, there is some risk that a prisoner could get loose. The cost of "house arrest" is balanced against the cost of housing low risk prisoners. While a net savings is realized, it is not large, and the funding must be justified separately.

Thus, there is a great need for an apparatus which would reduce, eliminate, or postpone the need for more prisons. Such an apparatus would accomplish tightened security of prisoner tracking, with virtually no risk of fooling the system, and would allow limited freedom of prisoners to rehabilitate themselves via controlled community interaction and limited freedom of travel. To state the obvious, a working taxpaying prisoner who is effectively restrained at little cost to the taxpayer is preferable to incarceration, where no true rehabilitation is accomplished and costs are becoming astronomical. Such a system is implemented with the present invention.

Additionally, some elderly or infirm persons need constant monitoring of their location and/or of certain medical parameters. Such parameters might include blood pressure, heart rate or the like. The present invention provides a means for accomplishing such a monitoring without the need for constant supervision and for providing immediate "real time" notification of the proper medical authorities. The system also provides a means for monitoring the status of an automobile in order to provide a deterrent to theft. For example, the apparatus can be attached to the car in some "hidden" spot to avoid or decrease the potential for removal. The motion, temperature, and position monitoring functions can then be used to detect theft or attempted theft of the auto. For example, the occurrence of motion or the detection of rising temperature might be indicative of the unauthorized starting of the car. With the position determining function, if the car is stolen, it can be tracked.

The invention disclosed herein overlaps several technical areas involving not only the provision of positioning data remotely of the sensor, but also of providing additional remote monitoring of other environmental factors such as temperature, audio signals, blood pressure, heart rate and the like.

One example of a prior art device providing relative positioning information is Kotoh, U.S. Pat. No. 4,673,936 issued Jun. 16, 1987. Kotoh discloses a rescue transmitter apparatus adapted to be worn on a person's wrist. Kotoh's transmitter transmits a microwave signal which may be received by a search and rescue craft. Relative position may be determined by using a directional antenna to determine the direction of the strongest signal. No absolute positioning or other, environmental information is available.

Another prior art device is illustrated in Darnell et. al. U.S. Pat. No. 5,043,736 issued Aug. 27, 1991. Unlike the Kotoh device, Darnell's transmits absolute, (i.e. geographical latitude and longitude), position information. Darnell discloses a hand held apparatus which contains both a GPS receivers as well as a cellular telephone transmitter. The hand held unit receives the GPS signals, generates a reference timing signal, and identifies the time difference therebetween. As is well understood in the art, this time difference is indicative of the distance between the receiver and the GPS satellite. Thus, from knowing the time differences from a series of satellites, an absolute position may be determined. This time difference information, determined by the hand held unit, is transmitted to a remotely located base unit. This base unit then uses the time difference information to determine the position of the remote unit. While the Darnell system is adapted to determine and transmit absolute positioning information, no other environmental information is detected or transmitted.

Several prior art devices have been proposed in the field of prisoner monitoring in the house arrest scenario. One of these is Pauley et. al. U.S. Pat. No. 4,885,571 issued Dec. 5, 1989. Pauley discloses a device (a "tag") which is adapted to be worn on the person subject to the house arrest. The device transmits periodically to a field unit which then communicates with a remotely positioned central processing unit. The communication of information from the "tag" to the field unit consists of an identification signal which is an encoded message identifying the "tag" from which the signal is sent. No other positional or other data is sent. Verification that the person is remaining within the prescribed limits imposed is inferred simply by the fact that the signal from the "tag" is being received by the field unit. Since the "tag" has a limited transmission range, reception of the signal transmitted therefrom by the field unit is possible only when the field unit is within the "tag's" transmission range. Thus, no absolute or even relative positioning data is available with the Pauley apparatus. Rather, a simple in-range/out-of-range indication is available.

U.S. Pat. No. 5,493,694 discloses a fast response system for a fleet of vehicles. At a selected time, a central station broadcasts an interrogation signal requesting that selected vehicles in a selected group respond with the present location and status of each vehicle. The central station then ceases its broadcasts and waits a certain time interval for the vehicle responses. Using a protocol known by the central station and by each of the vehicle transceivers, each vehicle replies with the requested information during a particular consecutive time slot. Each transceiver has listened to the central station's interrogation signal and knows (1) whether it was one of the transceivers queried, and (2) if it has been queried, what its numerical position in the queue for responding to the query. If a particular transceiver is not among those queried, the transceiver ignores the interrogation signal and waits for the next interrogation signal. In this way, only transceivers whose numbers are broadcast or otherwise identified respond to the central station, and each such transceiver responds only in its allocated time slot.

When the central station receives a call requiring assistance, it broadcasts an incident message that includes the location of the incident and whatever is known about the incident. Each vehicle message unit receives the incident message, determines its present location and the distance from that vehicle to the site of the incident, determines if that vehicle can respond to the incident, and replies to the incident message by transmitting its present location and other pertinent information. The vehicle message unit transmits this reply if and only if the distance is less than a predetermined distance to the incident site.

U.S. Pat. No. 5,528,248 to Steiner et al. discloses a personal digital location apparatus for displaying the consumer's location on a map. The device is a hand held apparatus having a GPS antenna and receiver to provide location information, and is capable of using standard operating systems to run existing applications, and is capable of running programs written in high level languages to provide the consumer with a display of his location and relative locations and the attributes of map features proximate to the consumer. Nothing is this patent relates to the continuous monitoring and tracking of an individual remote unit by a central control station.

U.S. Pat. No. 5,541,845 to Klein discloses methods for monitoring the adherence of a vehicle to a planned route and/or planned time schedule, within a selected corridor in location and time, where the vehicle follows a selected route. The invention may use GPS, or other location determination system, positioned on the vehicle, to determine and store the present location of the vehicle. The vehicle communicates its present location, route status (on route or off route), schedule status (on schedule, ahead or behind schedule), and other relevant information, to a central station from time to time. The processor in the vehicle attempts to locate the vehicle on the route by correlating the route and schedule data with the current time of day and current vehicle position. A snap-to-route command is provided to identify the location on the assigned route that is closest to the vehicle's present location as determined by the on-board location determination system. It should be noted in FIGS. 4 and 5, steps 39 and 49, that non-adherence to the specified route or failure to meet a specified time schedule will cause the vehicle system to notify the central station.

While this patent discloses an on-board computer which continuously tracks the location of the vehicle within a time/location schedule, and notifies a central station of any "violation" of either the time or location schedule, there is no provision for uploading particular parameters from the central station as to the route or "corridor" to be followed. Second, there is no provision for storage of a "map" of the track of the vehicle throughout the course of a day or selected time period, which is subsequently downloaded to the central control station so as to map out the specific time and location of the vehicle along the route.

U.S. Pat. No. 5,552,772 to Janky et al. discloses a location determination system used to determine the present location of a firefighter at a fire site or the like. In one embodiment, the firefighter carries a unit that receives signals from a group of sources. A central station interrogates one or more of the units, each selected unit automatically responding by transmitting its location to the central station for further processing, storage or display. The system can accumulate and report on the accumulated time a firefighter is present in one or more designated sub-regions at a site, and can advise a person at the control station that a particular worker should leave a sub-region when an accumulated time exceeds a selected threshold.

The patent discloses another polling type system which requires the central station to interrogate the remote units to determine the location of a firefighter. The remote units do not have processors which can store location data, nor upload parameters, nor download map information showing past locations.

U.S. Pat. No. 5,568,119 to Schipper et al. discloses a method and apparatus for monitoring the current location of a remote unit. The current location of the unit can be checked at selected time intervals. The device is particularly addressed to "house arrest" situations where an arrestee wears a location determining (LD) unit that receives signals allowing determination of the current location of the LD unit and arrestee. The signal sources may be GPS type systems or ground base systems. In one embodiment of the invention the remote unit processes the information to determine the present location of the arrestee and transmits this information to a central station. In another embodiment, the remote unit does not process the information, but rather transmits the information to the central station for further processing to determine the present location of the arrestee. The central station compares the present location of the arrestee with the designated site in its boundary to determine if the arrestee is staying on the designated site. If the arrestee has moved off the site without prearranged permission, or if no intelligible response signal is received at the designated times, the central station promptly notifies the appropriate authorities. The remote unit may contain a tamper detection circuit that transmits an alarm if tampering is detected. Optionally, the remote unit may transmit the present position information in encrypted form.

FIGS. 6 and 7 both show flow charts of a procedure used to determine the present location of an arrestee, and which include the initial step requiring the central station to transmit an interrogation signal to the remote unit. Thus, these flow charts disclose a polling type system, which polls the remote units at desired intervals. The remote units transmit location information, and the central station processes, stores and/or displays the location of the remote unit.

This patent also discloses the periodic modification of parameters to provide "corridors" or timed schedules, which the arrestee must follow. This information is processed at the central control station and alarms or warnings are transmitted from the central station for failure to comply with these parameters.

U.S. Pat. No. 5,461,390 to Hoshen discloses a locator device useful for house arrests and stalker detection. This device relies on a "polling" type apparatus, wherein a polling message is sent from a central location to remote units, to determine the location of the remote units at the time of "polling". There is no disclosure of any capability of Hoshen to upload parameters to the remote unit, store accumulations of location data as a "map" in the remote unit, nor to download a stored "map" to a central station. In addition, since the Hoshen apparatus is a polling type device, there is no "real time" alarm for violations of preset parameters.

U.S. Pat. No. 5,416,695 to Stutman et al. discloses a method and apparatus for alerting patients and medical personnel of emergency medical situations. The patent discloses the use of host connected by a telephone network to a "subscriber" unit, and receives information from a remote patient by a "telemetry" device. The remote telemetry device on the patient collects location information (via GPS) as well as medical information and transmits the information to the host computer. Parameters in the host computer are set, updated, or otherwise changed by the subscriber via the communications network. When the information transmitted from the patient exceeds these set parameters, a warning is sent both to the subscriber and to the patient.

A panic button is provided on the telemetry device permitting the patient to directly contact the host computer and thereby transmit an alert. It is noted that the typical method of providing information from the patients to the host computer is by "periodic polling" of all of the sources by the host computer. (See column 6, lines 3–5).

U.S. Pat. No. 5,416,468 to Baumann discloses a plurality of individual remote units on persons, which transmit the location of that person to a "field unit" at periodic intervals. If the information is not received at the field unit within a predetermined time range, an alarm may be triggered. The remote units may include "detectors" which sense environmental conditions and may transmit this data in addition to the location data to the field unit.

However, the Baumann remote unit can only transmit information, and does not know whether it was received by the field unit. Since no information may be received by the remote unit, it cannot receive any instructions as to differing parameters or the like. Finally, the remote unit does not store tracked accumulated information.

SUMMARY OF THE INVENTION

Consequently, it is a primary objective of the present invention to provide an apparatus and method of determining and displaying the absolute position of an individual remotely therefrom.

It is a further objective to provide an apparatus capable of sensing and transmitting environmental data such as audio, temperature, blood pressure, heart rate and the like.

An additional objective is to provide an apparatus capable of monitoring and transmitting medical data concerning an individual.

It is another objective to provide an apparatus which may be secured to an automobile in some "hidden" location and utilized to provide a deterrent to theft and a means for detecting a theft or attempted theft and tracking the vehicle thereafter.

A further objective is to provide an apparatus capable of use on persons in hazardous environments to monitor their position as well as the environment surrounding the person such as the level of radioactivity or the presence of poisonous gases or the like.

Yet another objective is to provide an apparatus which is capable of tracking military individuals carrying classified information between military sites such as missile silos and the like.

An additional objective of the present invention is to provide a method and apparatus for monitoring and tracking an individual, which will report non-compliance with predetermined parameters in real time.

Still a further objective is to provide an apparatus for continuously monitoring and tracking an individual which will store time stamped location information between transmissions of data to a host computer.

Yet another objective is to provide a method and apparatus of continuously monitoring and tracking an individual which permits a customer to redefine parameters retained in the remote individual units.

A final objective is to provide an apparatus which, as much as possible, utilizes off-the-shelf components.

An apparatus and method of monitoring mobile objects or persons of the present invention includes a remote unit adapted to be worn on the monitored person or object. These remote units would comprise the position and data sensors as well as the transmitter device to transmit the information back to a central tracking station. The remote units may be operative to monitor many data items such as system integrity, motion, temperature, audio, and the like in addition to position. This data would then be transmitted at predetermined intervals to a central monitoring station operative to process and display the information. The remote units have the capability of uploading new or revised parameters from the central tracking station, as well as storing time stamped location and environmental data between downloads of information to the central tracking station. Additionally, the remote units are capable of reporting non-compliance with the predetermined parameters in "real time".

DESCRIPTION OF THE PREFERRED EMBODIMENT

Figure 1:
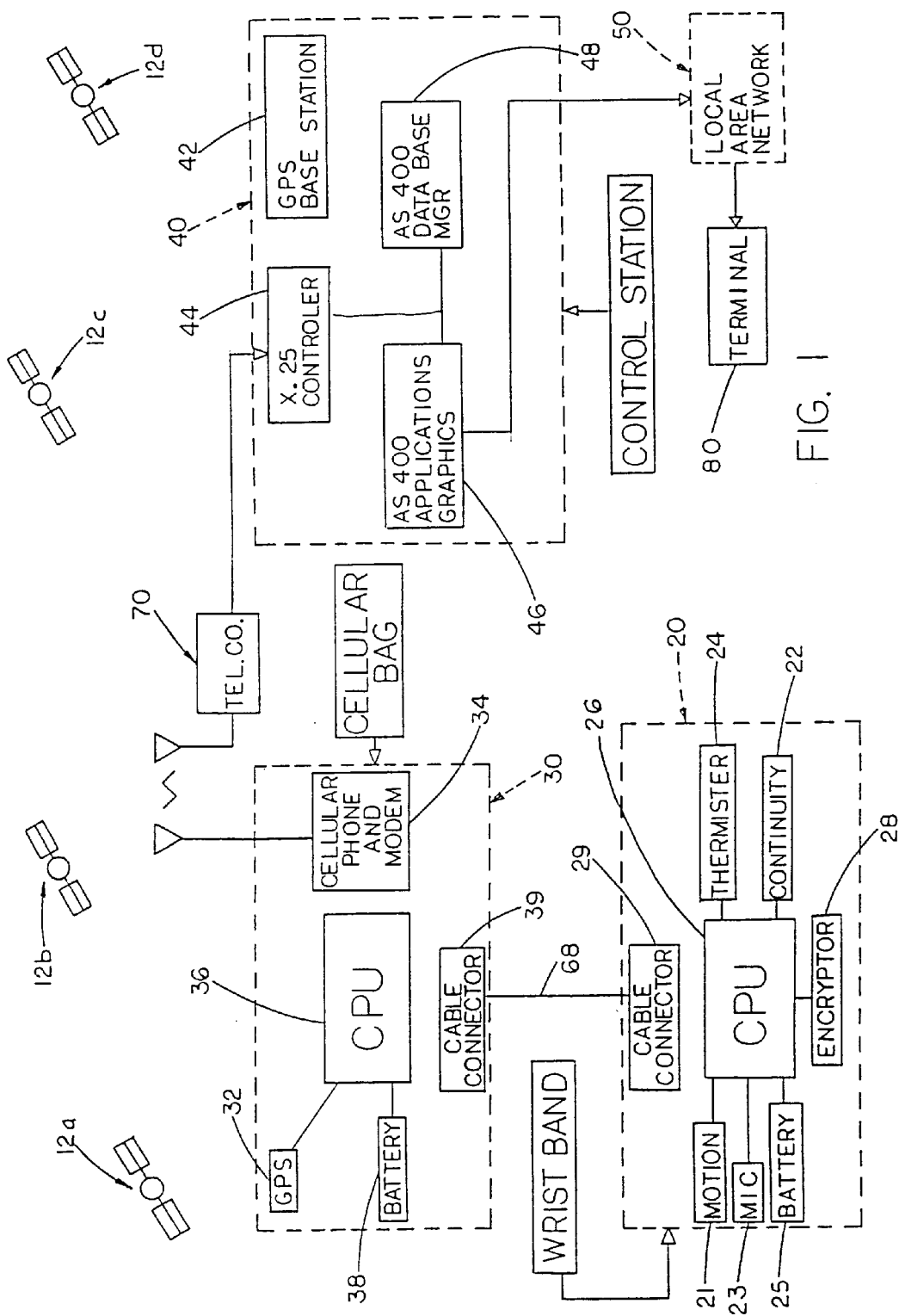
FIG. 1 is a block diagram representation of the major components of the invention.

1. General Background and Description of Operation

The goal of the present invention is to provide a means for tracking or identifying the geographical position of an individual and storing a "history" of that information. Another goal is to provide a means for monitoring certain medical or environmental information regarding an individual. Additionally, in some cases, it may be desirable to provide monitoring of both position and medical or environmental data.

The two most obvious uses for such an apparatus are in the "house arrest" and medical environments. To successfully accomplish these goals, the apparatus should be as small and as passive as possible. That is, no actions should be required of the monitored individual.

To accomplish this goal, the present invention merges two recent developments in navigation and communications, namely the Global Positioning System (GPS) and cellular telephone communications.

The GPS system in general is described well in other literature. Suffice it to say that GPS receivers can monitor from 4 to 8 satellites and accurately determine position to within a meter using differencing techniques. Accuracy of location improves as time passes and averages are taken. The typical receiver updates position every second and hence in one minute can accurately establish position. Initial time to acquire and establish position is longer, but this is done only on initial start-up or after a period of loss of signal for an extended time interval. The prisoner GPS receiver data would be monitored at intervals ranging from "always" to "as required", depending on the rules of enforcement.

The Central Tracking GPS receiver is used to establish correction data to correct for Selective Availability introduced error as well as other inherent errors in GPS technology. This correction data is constantly recorded with time stamp and is applied to all incoming tracking data from the remote units to correct incoming data for most accurate tracking.

Optionally, each remote unit may carry a receiver which picks up and supplies the GPS receiver with differential correction information. The correction data may be either an FM sub-carrier provider, or a government provided Beacon Correction information.

Cellular telephones are another recent technological advance greatly enlarging the amount of communication traffic which can be accommodated. As is well understood in the art, the cellular telephone system operates on the principle that numerous "cell sites" are scattered throughout a metropolitan area. Statistically, only a small percentage of telephones will be within a given "cell site" at any one time. Therefore, capacity can be increased by subdividing an area into these small "cell sites."

These technological advances are utilized by the present invention in order to provide the potential for large scale remote monitoring of individuals. The apparatus operates generally as follows. The monitored individual would "wear" a remote unit on his or her person. This remote unit would comprise the "monitoring components" as well as apparatus for transmitting the monitored information and receiving instructions. For example, if position is to be monitored, the remote unit would comprise a GPS receiver processor capable of receiving and processing GPS signals and determining a position therefrom.

Alternatively or additionally, if certain medical or environmental information is to be monitored, the remote unit would include apparatus adapted to monitor the desired parameter-such as temperature, motion, heart rate, blood pressure, radioactivity or poisonous gas level or the like. In either case, the information would be transmitted to a remote central control and tracking station for display, using wireless communications, such as a cellular telephone.

It is also contemplated that the remote unit may in fact be subdivided into two separate subcomponents. In the preferred embodiment, these subcomponents would comprise a "wrist band" and "cellular bag." The "wrist band" would be adapted to be worn on the wrist or around the ankle of the monitored person and would contain sensors to detect the medical or environmental information. The "cellular bag" could be worn around the waist, shoulder, etc. and would contain the apparatus for determining position and for transmitting the data. If the apparatus is to be used to monitor automobiles, the "individual worn" components would be secured to the auto, such as to the firewall and/or the steering column.

a. "Individual Worn" Components

In the preferred embodiment, the individual worn device consists of an ID bracelet, which contains a unique ENCRYPTION type responder, which returns a random encrypted code when queried. It also contains special conductivity wiring and circuits which validate that the unit has not been removed or tampered with, and is actually on a warm living body (via thermocouple and resistivity circuits and microphonics).

The ID bracelet connects to a small processor module contained within the "cellular bag" which acts as the overall processor for the prisoner system.

The processor module is worn on the belt, and contains the central processor, the communication equipment, in this case a cellular phone, and the detachable (but wire connected) GPS receiver. The basic function of the processor module is to provide monitoring of the ID bracelet, activation of the GPS receiver, the recording and storage of location data with a time and ID stamp, and control of the Cellular Phone.

In addition, the processor module has an audible and visual alert which the central processor can activate under pre-programmed rules, or via cellular control, for rule violations or the like.

The basic reporting implemented by the central processor to the prisoner or Central Control and Tracking station includes history of tracking information (Central Tracking), status of all hardware (Central Tracking), battery condition (prisoner audible and visual warning and Central Tracking), rule enforcement status (prisoner audible and visual warning if the rules of compliance are exceeded), and prisoner microphone monitoring.

Memory in the processing means is used for basic machine status logs. Tracking log and rule check logs would be nonvolatile and would remain intact in the event of a system failure, to validate a claim of failure by the prisoner.

b. Central Tracking Station Components

The central control and tracking station consists of multiple phone lines feeding into a switching hub, which in turn feed into an auto-dialing and data switching network, all controlled in the preferred embodiment by two or more IBM AS400 type computers. The first computer acts under the direction of the second to activate connection to the switching hub to acquire data or to respond to incoming data from the "individual worn" components, as required.

The first computer establishes and maintains a database on all individuals and the unique rules of compliance associated therewith as well as any violations. The second computer receives information from the first and displays the data graphically under control of monitoring personnel and according to preprogrammed format using a series of display terminals. This format can be tailored to the requirements of the individual monitored. Also controlled from the second computer are manning requirements and inter-departmental dispatch control.

It is anticipated that this system will track up to 4,000 or more prisoners, depending on the mix of types of rules enforcement. More restrictive rules requiring a larger percentage of resources would accommodate fewer individuals. Under minimal rule conditions, it is foreseen that only a few connections a day will provide effective control, as local broad rule enforcement and automatic call-in on violation require a minimum of resource utilization and very little personnel intervention.

c. Customer Location Components

In the preferred form of the invention, the customer may be the Department of Corrections (DOC). The customer is provided with at least one computer work station and is networked into the central tracking station by a dedicated fiber optic frame relay land line. Obviously, other equivalent means of communication between the customer and the central tracking station are possible, and contemplated by this invention. The customer, using customized software provided on the computer work station, has immediate access to their data base at the central tracking station at any time, via the land line. In this way, the customer may access all information relating to the monitoring and tracking of any specific prisoner, and may easily and immediately revise any rules of compliance for a particular prisoner. In addition, any violations of the existing rules of compliance will be transmitted from the central tracking station via the land line to the customer's work station, in "real time", to permit immediate reaction, if necessary.

d. Rules of Compliance

The phrase "rules of compliance" as used herein will refer to the limits imposed on a set of parameters assigned to each monitored individual. The rules allow a very broad range of tracking conditions, involving time, location, observation, and confirmation. In the preferred embodiment, these rules would be entered into a customer computer work station and then networked into the central control and tracking station as described above.

Typical rules of compliance for light enforcement would be to restrict the prisoner to the house during non-working hours, to allow travel to and from work, and limited travel with pre-arranged call-in for permission (hereinafter "inclusion" zones). Under these conditions, the central control tracking station would define the house on the computer to be a set of coordinates with a certain boundary. Actual verification would take place during an initial visit. Likewise, the route to and from work would be defined on the computer as a path with a certain width. Similarly, the workplace is defined by an initial visit.

At this point, the rules of compliance on how tightly the monitored person must stay within these bounds are devised by establishing how often the person will be monitored, and what response actions will take place if the person deviates from the plan. The actions are arbitrary and discretionary with the customer. For instance, if the customer is the Department of Corrections (DOC), it may wish to allow 5 minutes for the prisoner to self-correct a violation before dispatching an officer. Alternatively, the prisoner may be requested to call in when a violation has occurred. In other, more restrictive circumstances, the rules of compliance may require the central control and tracking station to dispatch an officer upon the immediate occurrence of any violation. In some cases, very loose travel rules may apply, with the limitation being on not allowing the prisoner to visit certain businesses, such as bars or other undesirable locations (hereinafter "exclusion" zone). These locations can be programmed in, monitored, and reported on. The variations are almost endless and are limited only by the ability of law enforcement to devise workable rules of compliance which make reasonable use of resources, are effective, and are agreeable to the courts.

In the preferred embodiment, certain safeguards are built in which assure security and integrity of the system. The bracelet has security devices built in which allow detection of any tampering and also allow environmental monitoring of audio, personal temperature, impact, motion and the like. Since a person moves constantly, even when sleeping, GPS and the motion detector combine to provide "dead man" monitoring, which automatically dispatches an officer if a lack of motion is detected for a prolonged period. A random alert call-in may also provide redundant verification. The person could, when alerted, call in and enter a code, all under computer control. A human operator would only be alerted if a problem occurred.

In general, rules of compliance would be scripted such that the court or DOC would define a level or class of monitoring, the limits of which could be established by prior agreement interdepartmentally. In addition, the DOC could have a set of discretionary rules which they could apply to fit the enforcement process to the individual. This information would be transferred to the central control and tracking station from the DOC, where a specific case file would be generated. The generated file would be printed as entered and returned to the DOC for validation. After validation, the prisoner would be a briefed, trained, and given a printed copy of the rules he would follow, which would be a signed photocopy of the validated DOC copy.

In the non-judicial monitoring situation such as medical monitoring, the functions operate in the same fashion. In the medical monitoring situation, the "rules of compliance" might comprise limits on heart rate, blood pressure or the like in addition to position monitoring. Any indication that any of the parameters were outside the limits of compliance could then be used to immediately dispatch appropriate medical help.

Alternatively, in the automobile monitoring situation the rules of compliance might be "no motion", "low temperature", etc. Indications of "rising temperature" and "motion" would be indicative of theft.

2. Preferred Hardware Design

The components comprising the present invention are best illustrated in FIG. 1. The major components of the present invention are divided into three categories. The first category includes the remote unit which is worn on the individual's person. The second category includes those components which reside at a central control and tracking station. These two groups of components are telephonically joined by the commercial telephone network preferably through the widely available cellular telephone system. The third category includes those components which reside at the customer location. As discussed above, the customer location components are networked to the central control and tracking station, preferably via a dedicated fiber optic frame relay land line.

In the preferred embodiment, the remote unit worn on the individual being tracked or monitored is further subdivided into two categories. The first remote unit, referred to as a "wrist band" 20, may be strapped to the individual's wrist or ankle as desired. This wristband 20 is in turn connected to the second category of individual worn components by a small electrical cable 68. The second remote unit maybe referred to as the "cellular bag" 30.

Cellular bag 30 comprises, among other components, a cellular telephone 34. It is this cellular telephone 34 which allows the remote units to be telephonically linked, through the commercial telephone network 70, to the central control and tracking station 40. As the name implies, the central control and tracking station 40 is the point where the data gathered by the remote units 20 and 30 is collected for display and analysis, and for further distribution to the customer location 90 (FIGS. 9–13 and 15).

As mentioned above, it is anticipated that many persons would be simultaneously monitored. Therefore, a central point such as central control tracking station 40 is the most efficient way in which to simultaneously monitor this plurality of persons. However, a means must be provided for systematically selecting from the incoming signals. Consequently, central control tracking station 40 comprises a communications controller 44 which is adapted to interface several different telephone lines simultaneously on a time multiplex basis. In the preferred embodiment, communication controller 44 is an X.255–500 line, wide band link card. One example of an acceptable X.25 standard card is the PC XNET card manufactured by QST of France. Wide band lines are available from the telephone company.

Figure 8:
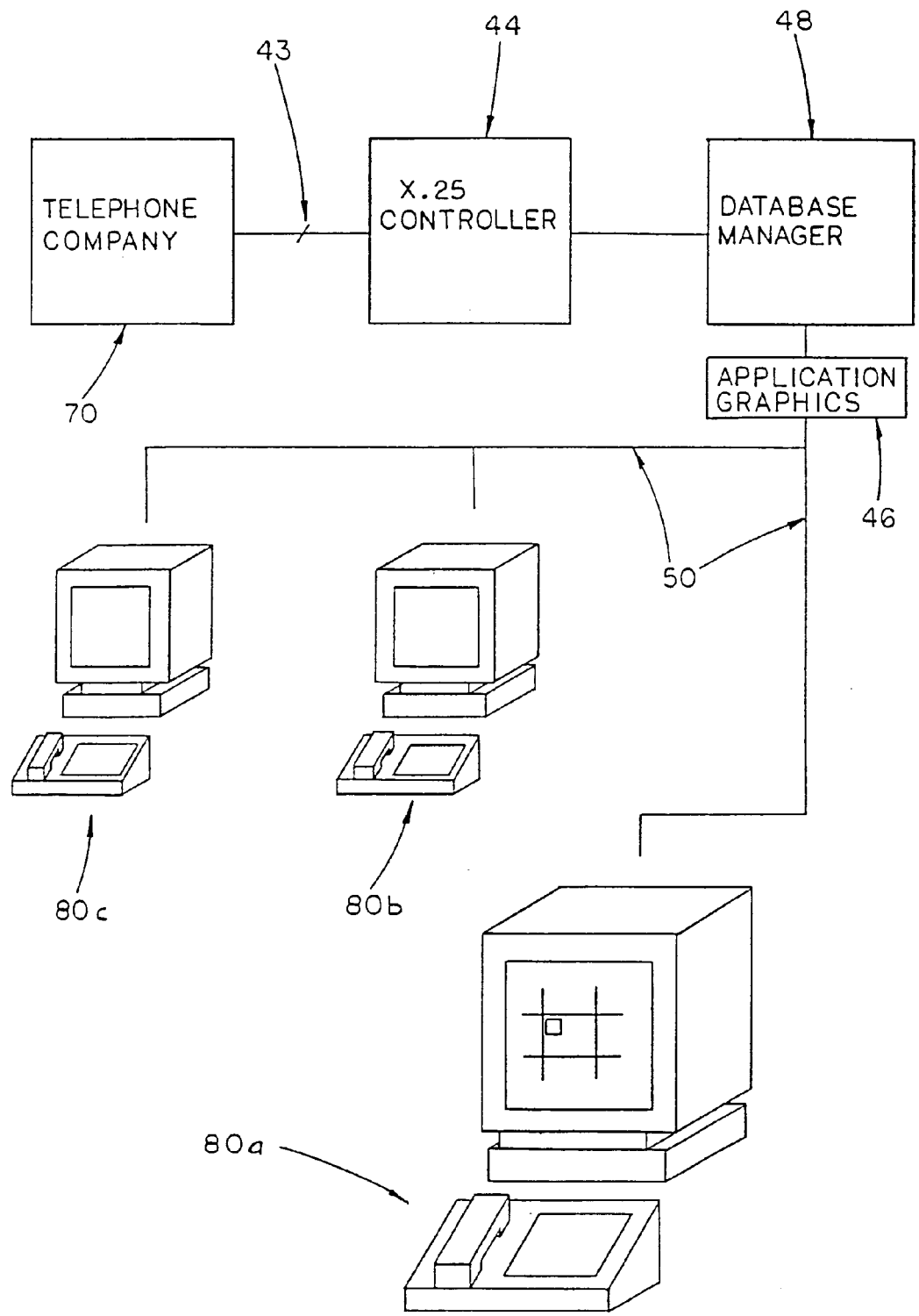
FIG. 8 is a pictorial representation of central tracking station components.
Figure 9:
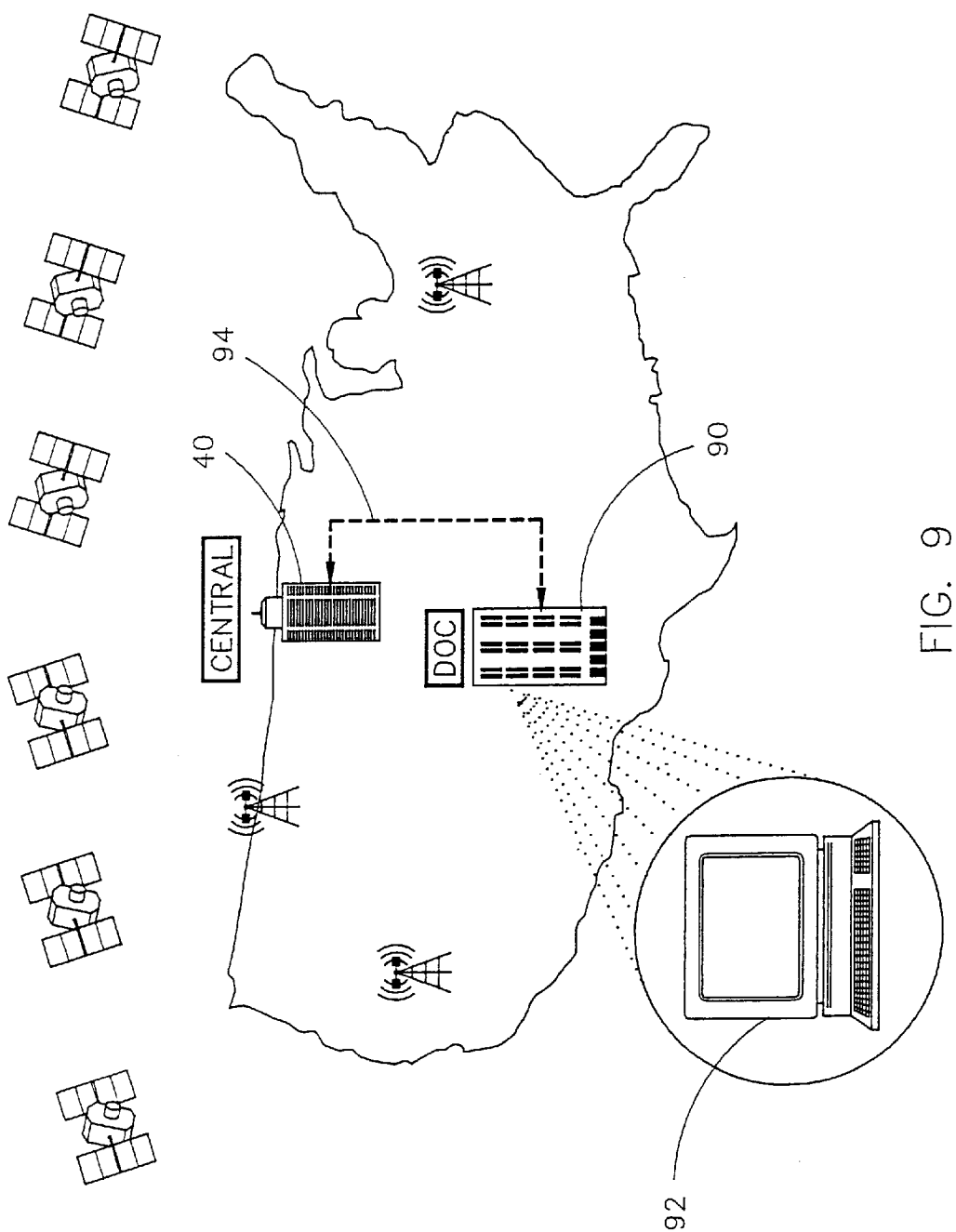
FIG. 9 is a schematic drawing showing the relation between the central control station and a customer.
Figure 10:
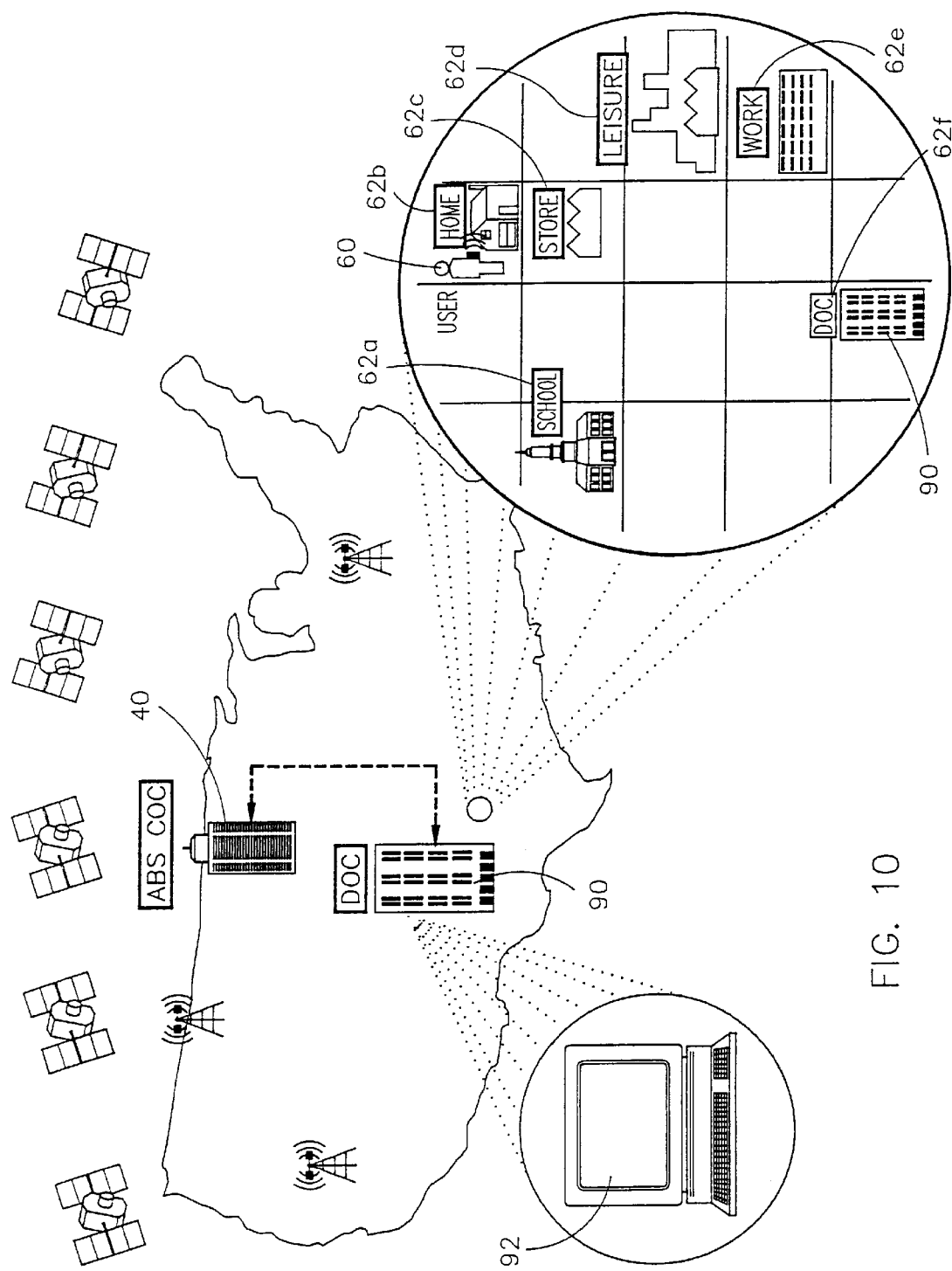
FIG. 10 is a schematic diagram showing the method of inputting the identification of specific activities to be monitored at a remote unit.

Central control tracking station 40 further comprises a computer processor which in the preferred embodiment is a plurality of stand-alone computer systems 46 and 48, adapted to interface with communications controller 44, receiving the telephonically transmitted data therefrom. It is anticipated that the functions of the two stand-alone computer systems 46 and 48 would be subdivided into applications graphics and database management functions, respectively. For example, the stand-alone computer system 46, responsible for graphics applications, can be used to provide a visual display to the operator of the geographic location of the person being monitored using data terminal in addition to printouts of the various data parameters being monitored. Additionally, computer 46 would be adapted to provide an alert indication to a series of terminals 80 connected through a local network 50, and to work stations 92 (FIGS. 9–15) at customer location 90, to identify any conditions where the rules of compliance have been exceeded. For example, if the remote unit fails to detect motion within a given time, this might be an indication of unconsciousness. Similarly, the individual worn apparatus might be programmed to monitor heart rate or blood pressure. As mentioned above, these items can be assigned tolerance limits within the rules of compliance held in memory of the processor in the cellular bag 30 and received from computers 46 and 48. In the preferred embodiment, terminals 80 may comprise a plurality of work stations (FIG. 8). Examples of displays which might be presented are shown and discussed below.

In the preferred embodiment, computer 48 is assigned the functions of database management. As mentioned above, it is anticipated that many persons would be monitored simultaneously by the present invention. For each of these monitored persons, a large group of data parameters would be monitored for compliance within pre-specified tolerance limits, the so called "rules of compliance" discussed above.

Also illustrated in FIG. 1 are the major components comprising the wristband 20 and the cellular bag 30. As indicated in the figure, the wristband 20 comprises a central processing unit 26 which has connected thereto a motion detector 21, an audio detector 23, a temperature detection 24 and a continuity detection 22. Also connected to central processing unit 26 is an apparatus for generating an encrypted identification signal 28. The purpose of encryptor 28 is to generate a unique, encrypted identification signal in response to a query from the central processing unit 26 or 36. This provides a means for the system to conduct an integrity check ensuring that the proper wrist band is installed. In the preferred embodiment, encryptor 28 comprises a model 1991 touch series of embedded identification chip manufactured by Dallas Semiconductor. In addition to the illustrated sensors, wrist band 20 may also include other sensors tailored to the given use environment, such as a blood pressure detector, heart rate detector, a radioactivity detector or a poisonous gas detector. The wrist band could either be equipped with the sensor itself or merely interface with existing sensors.

Motion detector 21 is electrically connected to central processing unit 26. In the preferred embodiment motion detector 21 is a conventional 2-axis, mercury switch, operative to detect motion of the wristband 20 of the system. The purpose for motion detector 21 is out of concern for the safety and well-being of the person being monitored. For example, the database management computer 48 and the central control tracking station 40 checks to ensure that the motion detector 21 has detected motion periodically. If the wristband 20 remains motionless for an abnormally long period of time, the monitored subject may have lost consciousness and be in need of medical attention.

Similarly, temperature detector 24 is electrically connected to central processing unit 26 and provides a means for monitoring the temperature adjacent wristband 20. It is assumed that the temperature sensed by temperature detector 24 should be approximately at body temperature and a reading to the contrary could indicate that the monitored person is in need of assistance. In the preferred embodiment temperature detector 24 may be a DS1620 thermistor manufactured by Dallas Semiconductor but there are many suitable substitutes. For example, Analog Devices also manufactures a unit which could also be utilized.

Figure 7:
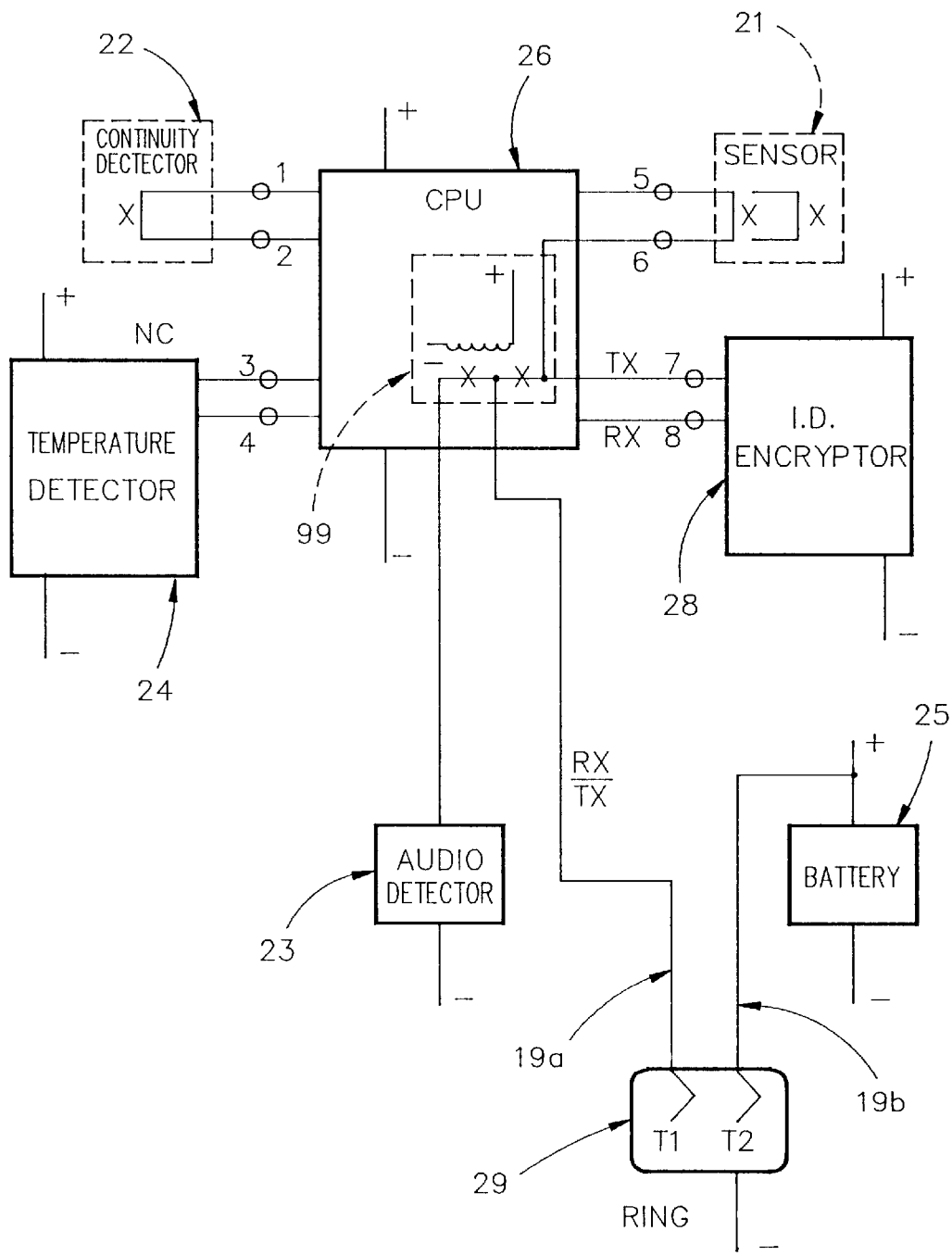
FIG. 7 is an electrical block diagram representation of the wrist band components.

Audio detector 23, also electrically connected to central processing unit 26, provides a means for the central control tracking station 40 to audibly monitor the individual. Thus, if the other environmental sensors indicate that a problem has occurred, the central control tracking station 40 can "switch on" audio detector 23 and attempt to determine the immediate situation. In the preferred embodiment audio detector 23 is a simple crystal microphone. Switching is accomplished by a relay available in the prototyping area 99 of the CPU board as discussed below (FIG. 7).

The final sensor indicated in FIG. 1 connected to CPU 26 is continuity detector 22. The purpose for continuity detector 22 is to determine whether the wristband 20 remains attached to the person, and immediately signals any removal or attempted removal thereof. This feature is probably most applicable in the judicial monitoring environment where a house-arrest prisoner may desire to remove the wristband 20 such that his flight from the prescribed geographic compliance limits remains undetected by the central control tracking station 40. There are several possible methods of accomplishing continuity detection, including resistivity and capacitance. In the present invention, resistivity is employed although others are equally well suited.

The goal of maintaining the connection integrity of the wristband 20 is further supported by the above discussed sensors. For example, if the continuity detector 22 for some reason should fail to detect a removal, the thermistor 24 would provide a backup indication since removal of the wristband 20 and the lack of proximity to the person's body would cause the temperature sensed by thermistor 24 to drop. Similarly, removal of the wristband 20 and placement on a stationary surface would be sensed by lack of motion detected from sensor 21. Thus, it can be seen that the various sensors incorporated in wristband 20 work cooperatively to ensure that the monitored conditions remain within prescribed conformance limits, or that any deviation therefrom is immediately identifiable.

The data values and statuses of the various sensors comprising wristband 20 are monitored and compiled by CPU 26. In the preferred embodiment, the CPU 26 associated with wristband 20 may be a "basic stamp" central processing unit manufactured by Parallax, Inc. This CPU comprises I/O and memory components as well as a 25K EEPROM which can be used to program the CPU. Clearly, many alternative CPU's are available which could perform the same functions, the criterion being one of individual preference so long as the CPU has I/O and memory functions and its physical dimensions will accommodate use in this environment.

The data signals collected by CPU 26 are transmitted to cellular bag 30 by cable 68 connected therebetween using connectors 29 and 39. It is anticipated that cable 68 would be a small co-axial or similar cable capable of establishing data communication therebetween. In some situations, it might also be desirable for cable 68 to comprise a conductor capable of transmitting power from cellular bag 30 to wristband 20. The status of this power line may also be monitored as another means of checking the security of wristband 20.

In some situations, it may be desirable for the connection between wristband 20 and cellular bag 30 to be wireless, thereby permitting a greater range of movement of the individual, while maintaining direct monitoring and tracking of the wristband.

The major components of cellular bag 30, as illustrated in the figure, include the global positioning system (GPS) receiver 32, the central processor unit 36 and the cellular phone and modem communication apparatus 34. In addition to the components illustrated, bag 30 may also include an ID encryption circuit 84 shown and discussed in connection with FIG. 5. The GPS receiver 32 is operative to receive the ranging signals transmitted by global positioning satellites 12a–d which are in geosynchronous orbit about the earth. In the preferred embodiment, GPS receiver 32 is an "Oncore" unit manufactured by Motorola, Inc. As is well understood in the art, GPS receiver 32 is capable of receiving the ranging signals from the GPS satellites and converting this information into a geographical latitude and longitude. This information may then be transferred to and used by CPU 36.

In the preferred embodiment, CPU 36 is a "Micro 44E" programmable microcontroller manufactured by Blue Earth Research, Inc. In addition to the positioning information form GPS receiver 32, central processing unit 36 may include an interface operative to receive and process the data acquired by the wristband sensors including continuity and other environmental data.

The basic parameters which the CPU 36 may monitor include position determination interval (from 1 per second to some arbitrary interval), position violation as a function of location and time (broad rules for unmanned tracking), battery condition, ID bracelet status (continuity etc.), cellular phone availability status (monitor for valid dial tone at programmed interval), valid communications status (code key passing), GPS system status (loss of signal from preprogrammed minimum number of satellites), special rule enforcement and validation (harsh environment check in procedures), loss of coverage rule enforcement (loss of cellular or GPS time-out), microphone activation (Central Tracking random or special monitoring rules) and miscellaneous environmental data.

As mentioned, data from wristband 20 is transmitted to cellular bag 30 and central processing unit 36 through cable 68. CPU 36 may include an interface means to facilitate the reception of this data. All of the sensed data, including positioning data from GPS receiver 32 and environmental data from wristband 20 sensors reside in central processing unit 36. Central processing unit 36 is electrically connected to cellular phone and modem communication apparatus 34. In the preferred embodiment, cellular phone and modem communication apparatus 34 is a model RS 17-1061 cellular telephone and attached data kit 17-1617 manufactured by Radio Shack but many other suitable alternatives are available. Cellular phone and modem communication apparatus 34 thus allows the positioning and environmental data collected by central processing unit 36 to be transmitted by conventional cellular transmission to the telephone system 70 and then by conventional telephone to central control tracking station 40.

CPU 36 also includes data processing functionality for a variety of purposes. First, various rules of compliance parameters for geographical limits on inclusion zones and exclusion zones, as well as time intervals for downloading of stored information to the control and tracking station, may be uploaded from the central control tracking station 40 via communication apparatus 34. Second, CPU 36 includes memory in which the sensed data, including time stamped geographical position, is stored until the occurrence of the next scheduled download to the central control tracking station 40. Finally, CPU 36 will continuously compare the position data from the GPS receiver with the rules of a compliance data received from central control tracking station 40, and give a "real time" alarm signal upon the violation of any rule of compliance. This alarm signal is immediately transmitted to the central control tracking station 40, for further processing and distribution to the customer location 90. Thus, CPU 36 is not merely a "dumb" transmitter, but is rather an interactive "intelligent" microprocessor.

As noted above, the bag 30 may also include a receiver for differential correction information, which is electrically connected to CPU 36. Thus, CPU 36 may make the necessary differential correction of GPS signals to determine position more accurately.

Electrical power for the remote units is primarily provided by battery 38 in bag 30. Battery life would be less with strict rule enforcement, since more frequent transmissions of data are required. Conversely, battery life would be longer with less stringent enforcement since less frequent transmissions are required. The battery would be of the quick-charge type and removable, with the prisoner responsible for monitoring and replacing as required. The system would give a time warning to the prisoner via lamp 82 (FIGS. 3–5) indicating pending battery depletion. In the preferred embodiment, an internal buffer battery would supply 5–10 minutes of function without the main battery pack. This interval would give the prisoner time to call Central Tracking if for some reason battery replacement failed, resulting in an imminent rule violation and requiring field service. In this situation, a lock-down mode is envisioned which would require that the prisoner remain at the last reported position until service arrived.

Figure 2:
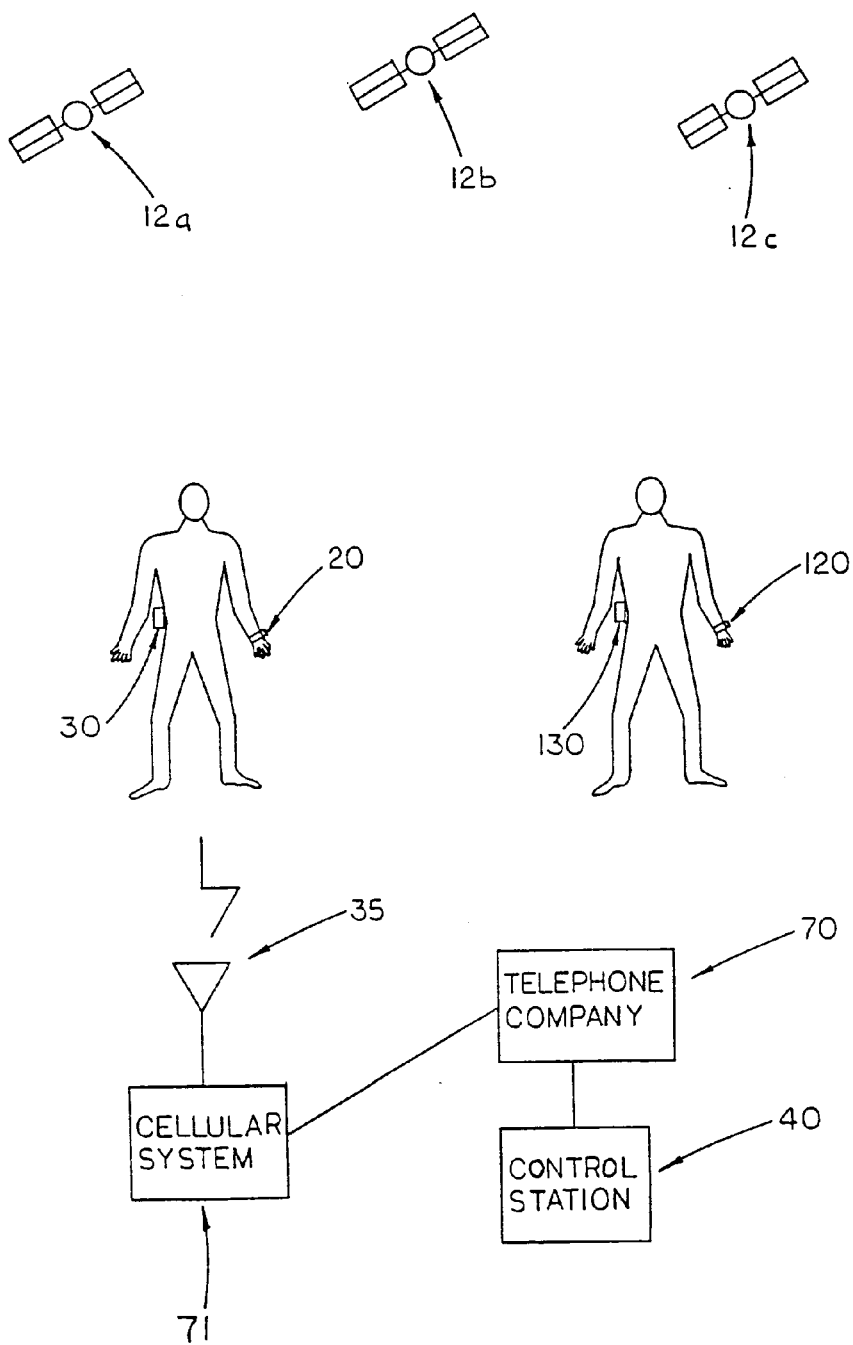
FIG. 2 is a pictorial representation of the overall operational environment of the system.

FIG. 2 is a pictorial representation of the environment in which the tracking and monitoring apparatus of the present invention is used. As seen in this figure, the preferred embodiment of the apparatus comprises wristbands 20 and 120 and cellular bags 30 and 130 which are adapted to be worn on the wrist and waist, respectively, of the monitored individuals. As seen in this figure, it is envisioned that the apparatus would be employed on a number of individuals. As mentioned above with reference to FIG. 1, bags 30 and 130, receive positioning signals from GPS satellites 12a–d. Cellular bags 30 and 130 also receive environmental data from their respective wristbands 20 and 120. Cellular bags 30 and 130 also receive rules of compliance parameters and other downloading information from control station 40 via the cellular telephone system 71. The accumulated time stamped position data, and various environmental data is then downloaded at desired intervals from the cellular bags 30 and 130 by the communication apparatus 34 (shown in FIG. 1). In the preferred form of the invention, the communication apparatus is cellular telephone, which is linked to telephone central office 70 via a cellular telephone system 71. The telephonically transmitted data would then be available to the central control tracking station 40 and customer location 90 by means of conventional telephone land lines.

Figure 3:
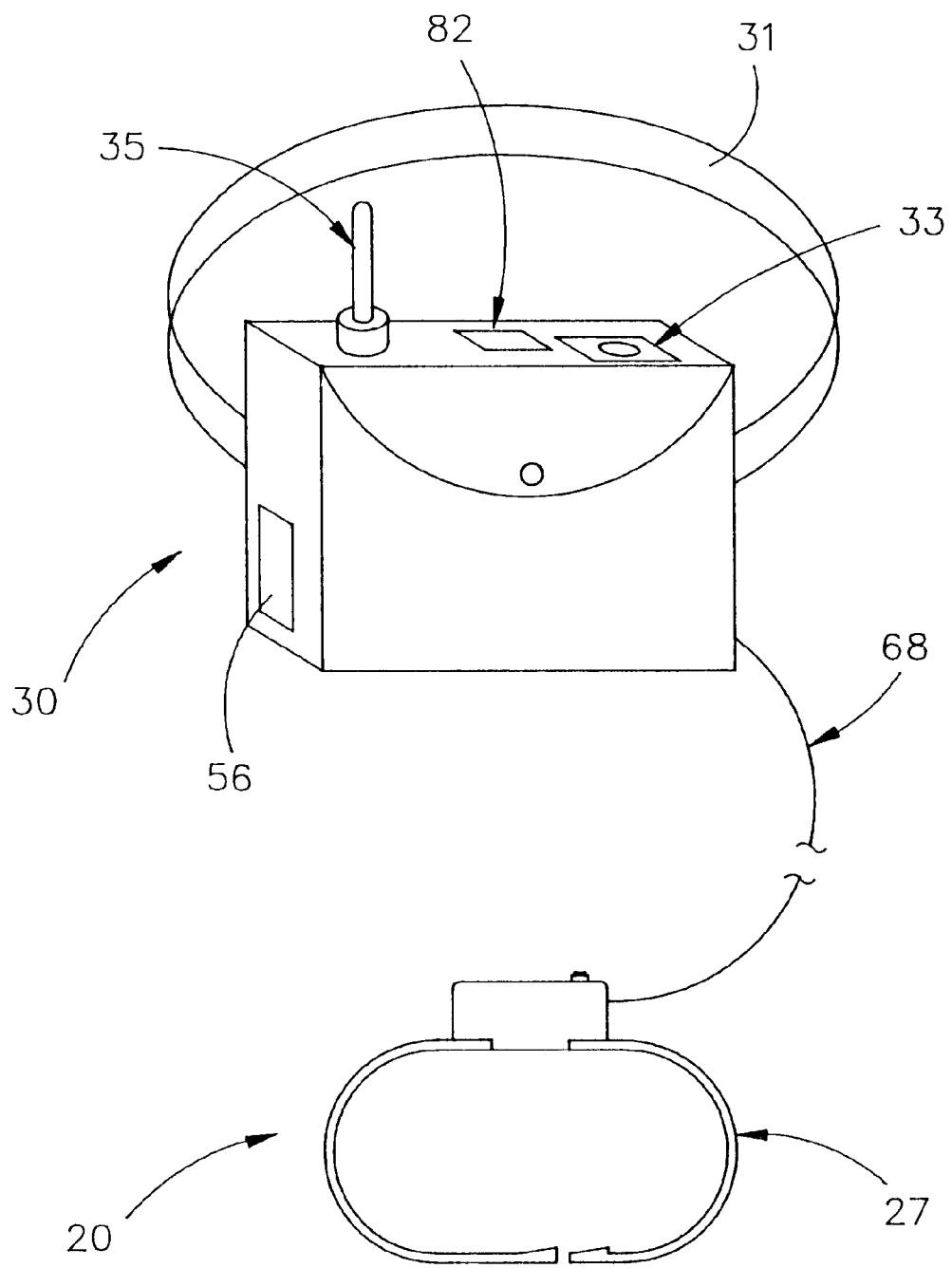
FIG. 3 is a pictorial representation of the cellular bag which would be worn by the individual and its interconnection to the wrist band.

FIG. 3 is a pictorial representation of the cellular bag 30 and associated external components and the connection to wristband 20. As seen in this figure, the major external identifiable components of cellular bag 30 comprise the waist or shoulder strap 31, the cellular antenna 35, and the GPS receiver antenna 33. The cable 68 is illustrated connecting the cellular bag 30 and the wristband 20 as discussed above. Cable 68 is operative to connect cellular bag 30 and wristband 20 providing communication and/or power therebetween. Lamp 82 is provided on the outside face of bag 30. Lamp 82 may be provided to alert the monitored person to an alert condition such as position violation as well as battery low condition or the like. Speaker 56 is provided to give an audio warning in addition to the visual warning provided by lamp 82. Also shown in the figure is the wrist strap 27 used to maintain the wristband 20 in position. Strap 27 also functions as a continuity strap used in conjunction with continuity detector 22 in order to provide an indication of removal or attempt at removal of the wristband 20.

Figure 4:
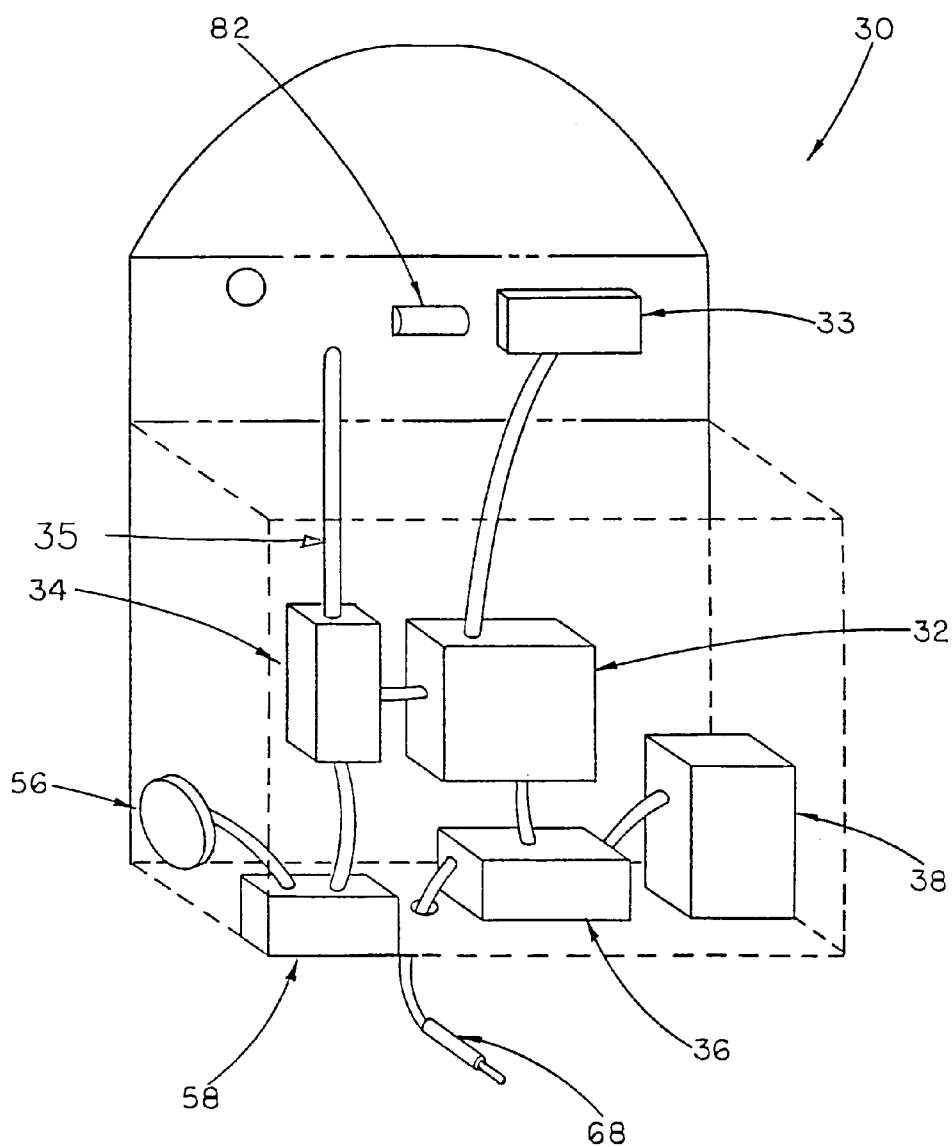
FIG. 4 is a pictorial representation of internal components of the cellular bag.

FIG. 4 is a further enlargement of some of the internal components of cellular bag 30. Illustrated in this figure are the GPS receiver 32, the internal components of the cellular antenna 35, the cellular phone and modem communication apparatus 34, the connection cable 68, the central processing unit 36 and the GPS antenna 33. Also shown are the sources of electrical power for the "individual worn" components, namely batteries 38 and 58. Finally, the figure illustrates speaker 56 and lamp 82. Speaker 56 and lamp 82 are used to provide an indication to the monitored person that he has exceeded compliance limits. In the "house arrest" situation, depending on the severity of the crime, the individual might be provided a certain limited time to correct the violation prior to action being taken. Speaker 56 and lamp 82 provide him with both a visual and audio indication that this "grace period" has begun.

Figure 5:
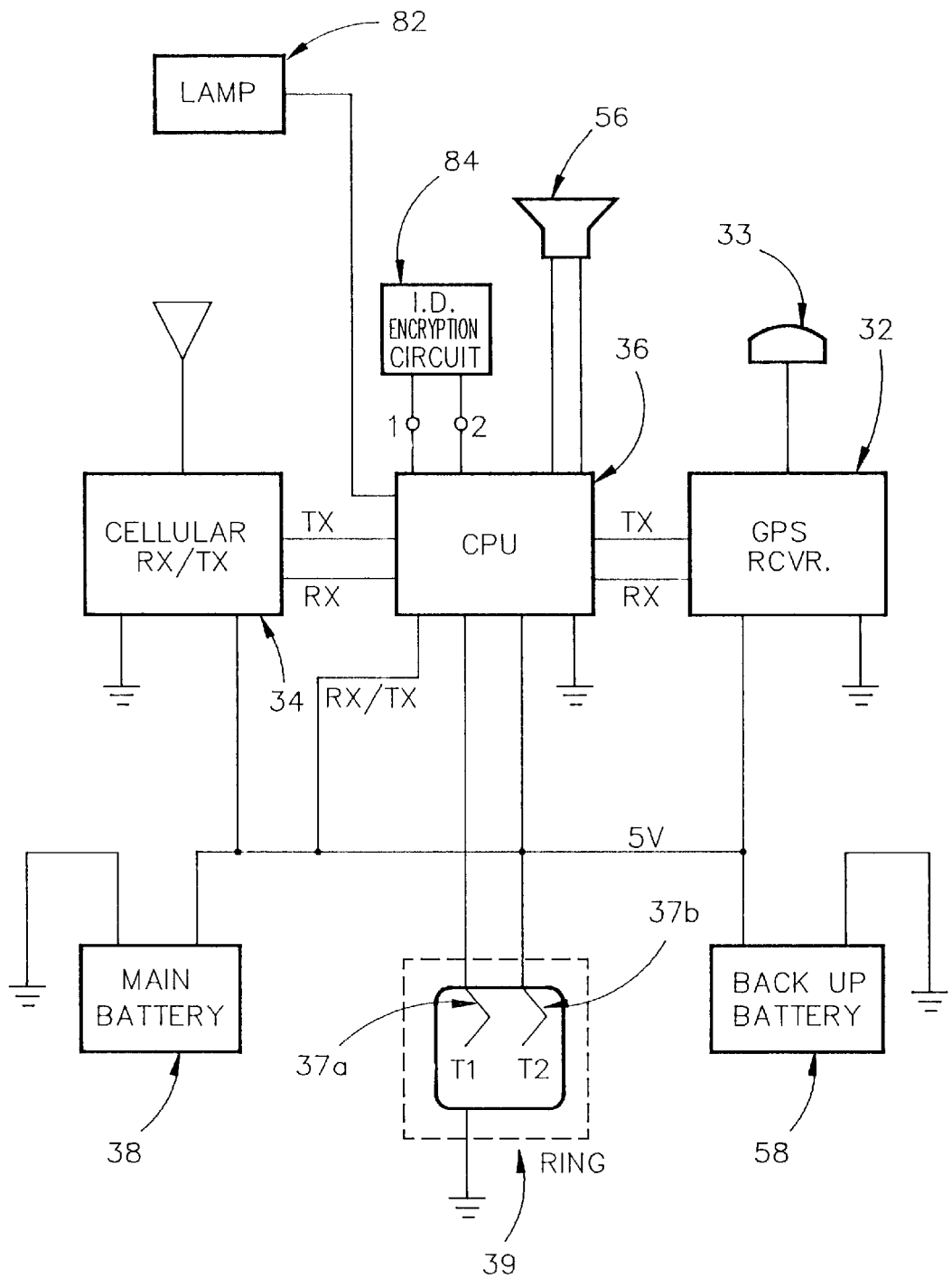
FIG. 5 is an electrical block diagram representation of the cellular bag components.

FIG. 5 is a schematic representation of the major components making up cellular bag 30, showing in particular the electrical interconnections therebetween. Cellular phone and modem communication apparatus 34 is illustrated with the transmit and receive line to the cellular bag central processing unit 36. Similarly, GPS receiver 32 is shown connected to central processing unit 36 by means of receive and transmit lines. These receive and transmit lines between the cellular phone and modem communication apparatus 34 and GPS receiver 32 establish data communication links with central processing unit 36.

ID encryption chip 84 operates in a fashion similar to ID chip 28 in wrist band 20. Namely, it provides a unique identification symbol when requested by CPU 36. Thus, encryption chip 84 provides another layer of security that the proper bag/wrist band combination is connected.

Also shown in FIG. 5 are the batteries 38 and 58 used to make up the electrical supply for the components comprising cellular bag 30. FIG. 5 illustrates the connection 39 associated with cellular bag 30 used to establish data and power communication with wristband 20. Also shown are speaker 56 and light 82 which may be used to provide an "out of compliance" indication as well as a "battery low" indication. Finally, shown as parts of cable connector 39 are jacks 37a and 37b which are used for data reception and power supply, respectively.

Figure 6:
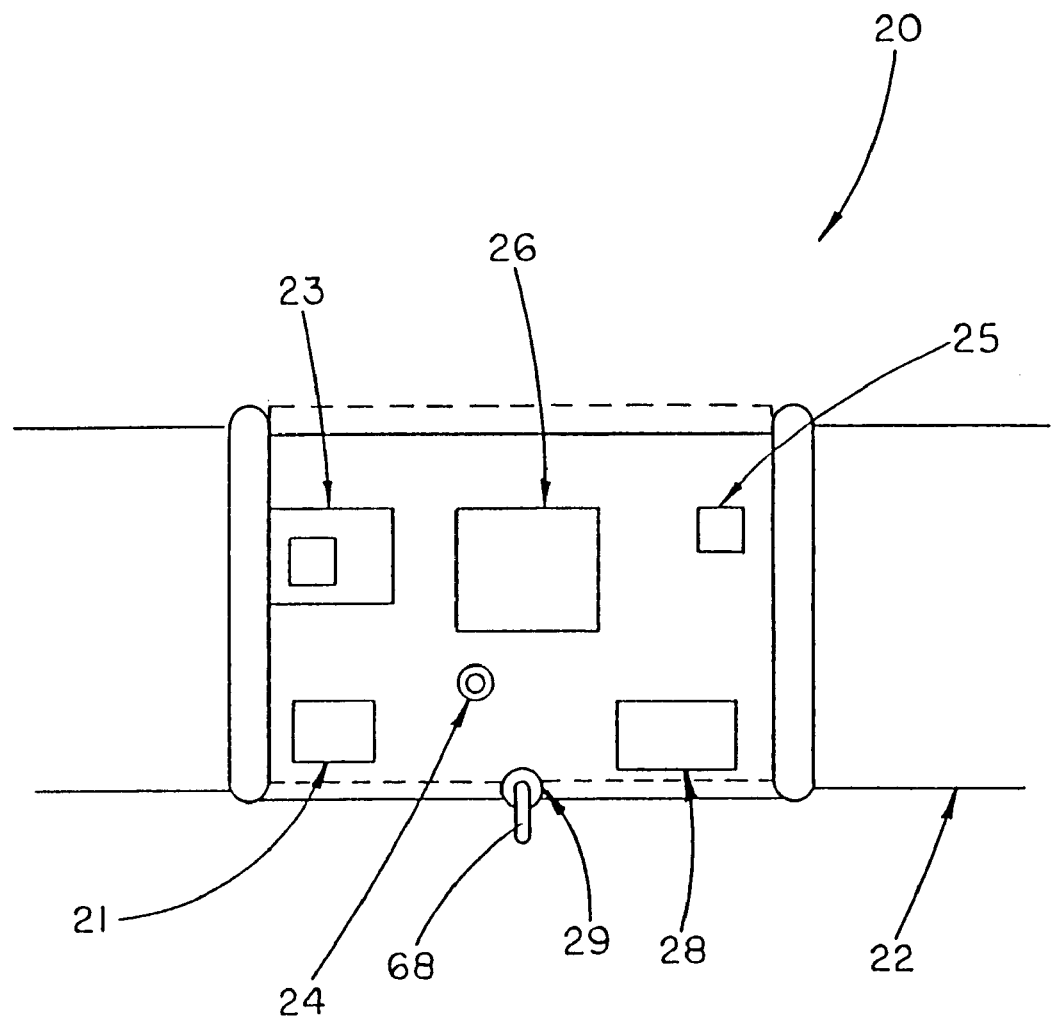
FIG. 6 is a pictorial representation of the wrist band components.

FIG. 6 is an enlarged pictorial representation of the major internal components of wristband 20. As indicated in this figure, the wristband internal components include microphone 23, central processing unit 26, motion detector 21, identification encryptor 28, continuity detector 22, and thermistor 24.

Microphone 23 is used to allow audio monitoring of an individual in case some discrepancy or abnormality in the monitored data is detected. As described above, the preferred processing unit for CPU central processing unit 26 may preferably be the "basic stamp" CPU manufactured by Parallax, Inc. This CPU has I/O, and memory components including a 25K EEPROM. It will be understood by those in the art that the "basic stamp" computer board contains a "scratch pad" or "prototype" area 99 which is adapted to receive the microphone 23 and a relay which is able to switch between transmission of digital information and the audio signal from microphone 23 (see FIG. 7 below).

Identification encryptor 28 may be a No. 1991 "touch series" of embedded identification chips manufactured by Dallas Semiconductor as shown in FIG. 6. Also illustrated in this figure is the cable connector 29 used to connect the wristband 20 to the cellular bag 30 by means of cable 68. As mentioned above, microphone 23 may be a simple crystal microphone which is adapted to be received on the "basic stamp" microcomputer. Thermistor 24 may be a conventional model DS1620 manufactured by Dallas Semiconductor.

FIG. 7 is a more detailed schematic diagram illustrating the data and power communication within the wristband 20. As illustrated in this figure, the central processing unit 26 is electrically connected to temperature sensor 24. Thus, temperature data sensed by sensor 24 may be transmitted to central processing unit 26 for later transmission to cellular bag 30 via cable 68. Additionally, the central processing unit 26 is electrically connected to identification encryptor 28 through receive and transmit lines as indicated.

As mentioned above, the encryptor 28 is operative to generate and transmit a unique and encoded identification to the CPU 26 which may then be forwarded to the cellular bag 30 and on to the central control tracking station 40. Identification encryptor 28 provides a means for identifying the particular wrist band 20 connected to bag 30 preventing the exchanging of wristbands between different monitored individuals or bags. Also shown are the motion detector 21, microphone 23, and continuity detector 22 and their interconnection to central processing unit 26. As mentioned above, the preferred embodiment for the motion detector 21 is a 2-axis mercury switch. The resistivity-based continuity detector 22 is made up in part by the band 27 and its interconnection to the wristband 20. Finally, the cable connector 29 for connecting data and power communication cable 68 to wristband 20 from cellular bag 30 is illustrated. As shown in the figure, the cable connector 29 includes both a data line 19a as well as a power line 19b.

As will be understood by those in the art, the "basic stamp" CPU 26 includes a prototype area 99 adapted to switch between various connections for output using a relay switch. In the present invention this switching is used to switch the receive/transmit line 19a to microphone 23 enabling its output.

FIG. 8 is a pictorial representation of the central control tracking station 40. As illustrated in this figure, the positioning and environmental data are downloaded to the central control tracking station 40 by means of the conventional telephone central office 70 through a series of land lines or wide-band co-axial cable 43. This plurality of incoming signals are fed to X.25 controller 44. In the preferred embodiment, the X.25 controller is a 500-line time demultiplexer similar to that used on commercial and private bulletin boards for interfacing the central control tracking station 40 to a large number of incoming telephone lines. As mentioned above, one suitable controller is the PC Xnet card manufactured by OST. After demultiplexing, the signal may be fed into the application graphics computer 46 and database management computer 48.

As mentioned above, the database management computer 48 in the preferred embodiment would be an IBM AS400 computer. Clearly many other commercially available computers would be equally suitable. The purpose of database management computer 48 is to collect and manage incoming data from the telephone lines and from various customer locations 90 via land lines 94. The data from database management computer 48 may be directed to applications graphics computer 46, customer location 90 and/or uploaded to the cellular bags.

In the preferred embodiment, this graphics computer 46 may also be an IBM AS400. Applications graphics computer 46 processes the data from computer 48 to formulate displays in response thereto. After processing by graphics computer 46, the information is transmitted to a plurality of work stations 80a–c for display to the operators. As mentioned above, the purpose of applications graphics work stations 80a–c is to visually display the data received and in particular to identify any alerts resulting from non-compliance with prescribed limits.

Referring now to FIGS. 9–15, an example of use of the method and apparatus of the present invention is described in more detail. In this example, the customer is the Department of Corrections (DOC), with the customer location designated generally at 90 and located remote from the central control station 40. As discussed above, central control station 40 is connected to customer location 90 such that information may be easily and accurately transmitted therebetween. Preferably, the connection is by dedicated fiber optic frame relay land line, and the customer location preferably includes a computer work station 92 permitting the receipt and display of information as well as allowing the input of information into the system. It should be understood that more than one customer may be directly connected to central control station 40, throughout the geographic territory. It should also be understood that many other means for networking the central control station with the particular customer may be employed within the scope of this invention.

The initial step in the method of the present invention (FIG. 10) calls for the customer to identify a particular user 60 and the geographic locations of the various activities 62a–62f, which the user will contact. In the case of a "house arrest", these activities may include school 62a, home 62b, a store 62c, various leisure activities 62d, work 62e, and the probation officer at the Department of Corrections 62f. All of these activities are input into the system via work station 92 at the customer location 90, and networked to the central control station 40.

Figure 11:
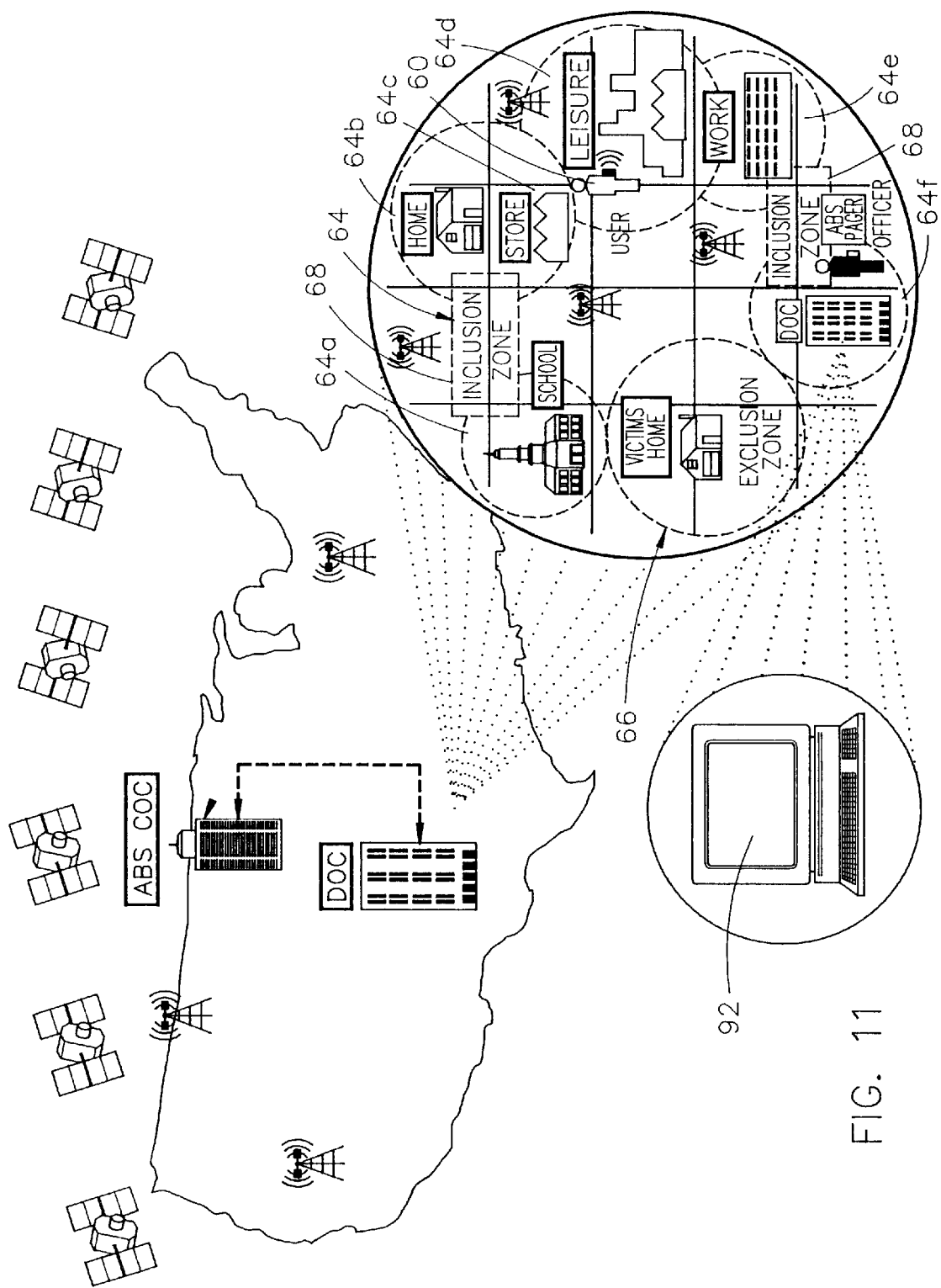
FIG. 11 is a schematic diagram showing the process of inputting geographic locations and time constraints for the activities identified in FIG. 10.
Figure 12:
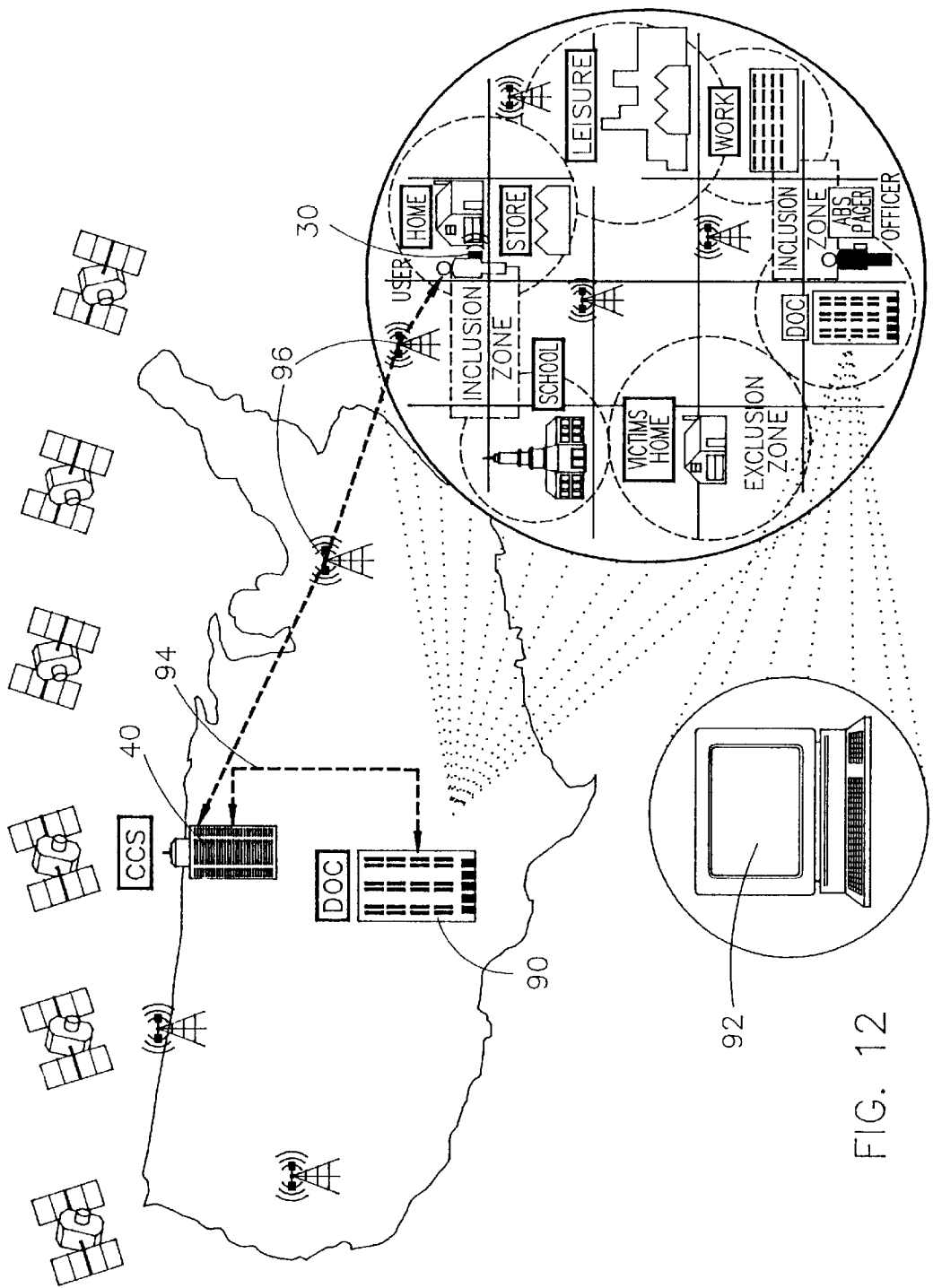
FIG. 12 is a schematic diagram showing the method of uploading parameters to a remote unit.

Once the activities have been identified, the customer will enter individual geographic locations and time constraints using work station 92. These locations and time constraints are generally identified as "inclusion" zones 64 or "exclusion" zones 66 (FIG. 11). Each inclusion zone identifies the geographic parameters of the allowable activities of an individual user 60 (shown as zones 64a, 64b, 64c, 64d, 64e, and 64f respectively). In addition, corridors 68 are provided between various inclusion zones to permit travel by the user between these zones. An exclusion zone 66 would include locations such as a victim's home, or possibly bars, race tracks, or other identifiable locations for which the particular user 60 is restrained from contact.

Once the data has been entered into the customer computer work station 92, it is networked into the central control station 40 through the fiber optic frame relay line 94. Once the remote unit or cellular bag 30 is activated, the various parameters, or "rules of compliance" are uploaded from the central control station 40 directly to remote cellular bag 30. Preferably, this uploading occurs via cellular telephone towers 96 (FIGS. 12 and 15), as described in more detail hereinabove. These parameters may be modified as needed by the customer in the same fashion, with uploads occurring by way of central control station 40 to remote cellular unit 30.

Figure 13:
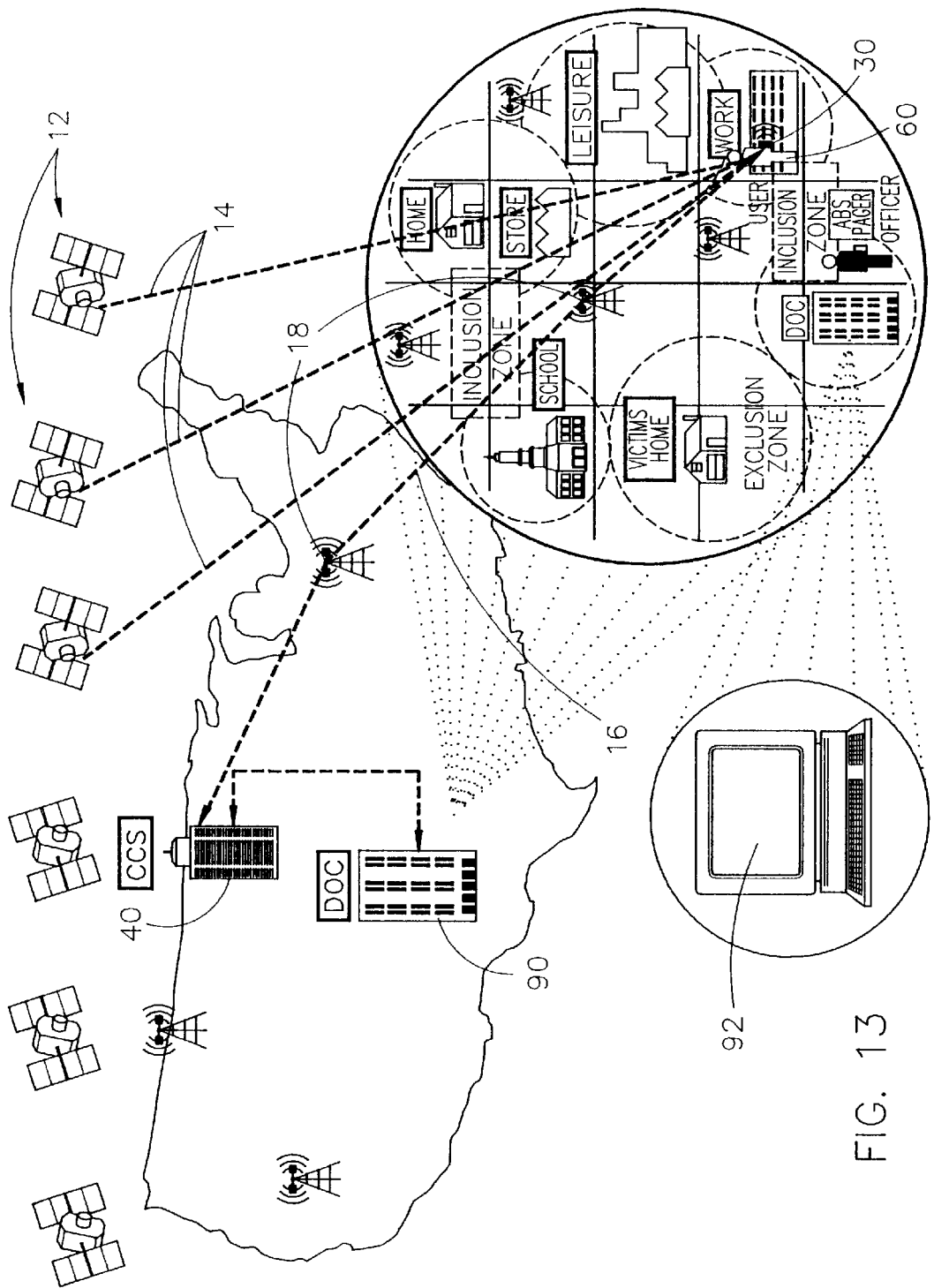
FIG. 13 is a schematic diagram showing the process of downloading monitored information.

Referring now to FIG. 13, the process for downloading standard monitoring and tracking information is shown. Part of the information which is uploaded to remote cellular unit 30 is a schedule identifying the periodic times for the standard download of monitoring and tracking information. As described above, remote unit 30 receives GPS signals from a plurality of satellites 12 to determine the geographic location of the user 60. Typically, the GPS receiver in remote unit 30 will update this position determination every second. This position information is continuously recorded with a time stamp and stored within the CPU in remote 30 until the predetermined time for an intermittent standard download of information. Broken line arrows 14 indicate the transmission of GPS signals from satellites 12 to remote unit 30 for the accurate determination of the location of user 60.

The download of data stored in remote unit 30 to central control station 40 is preferably by cellular telephone, and is generally indicated by arrow 16, extending from remote unit 30 through cellular towers 18 to central control station 40. The standard informational downloads are then processed and stored at central control station 40, and transmitted to the customer location 90 at predetermined intervals, determined by the customer.

Figure 14:
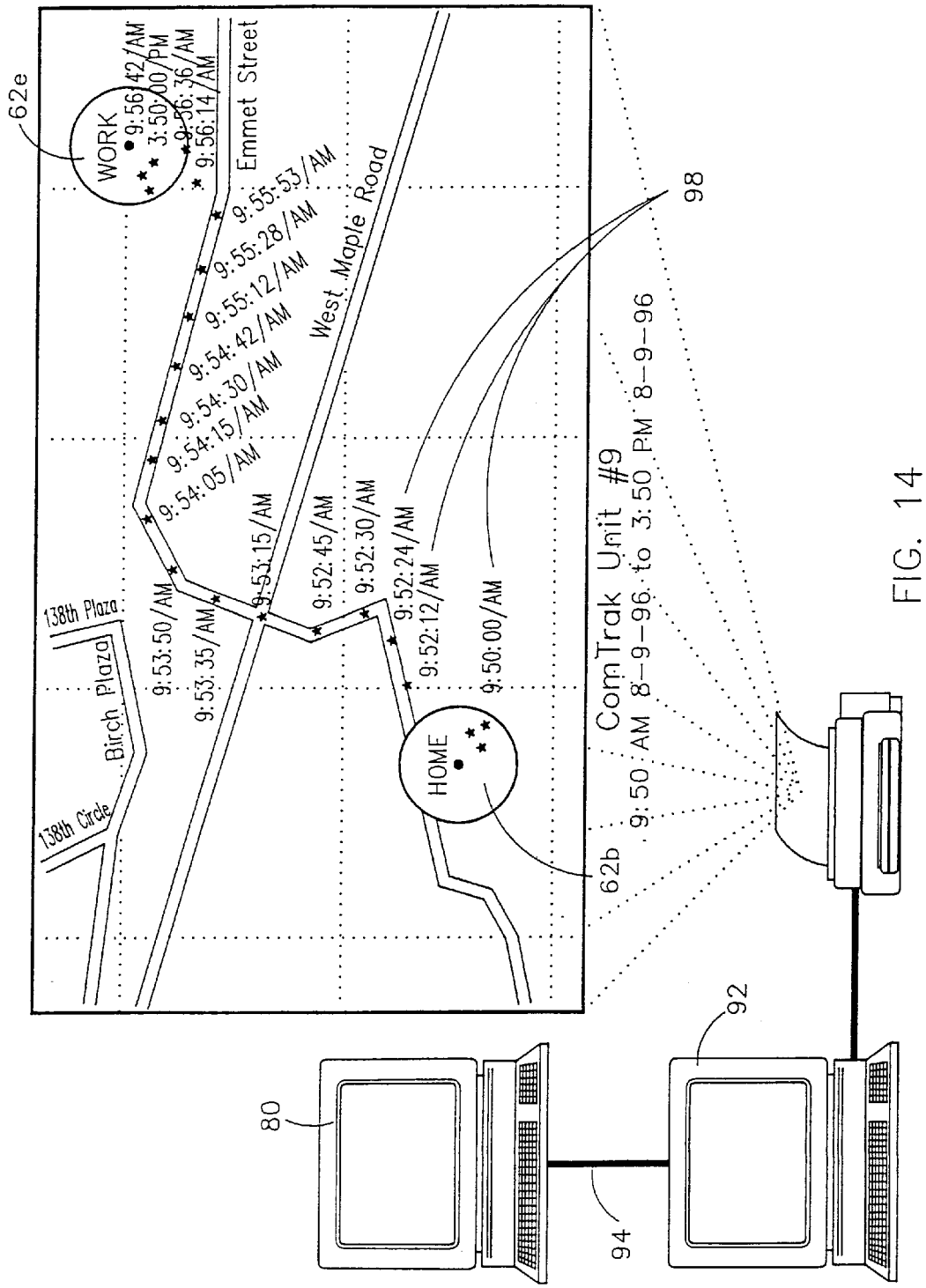
FIG. 14 is a schematic diagram showing the display of downloaded information from the remote unit.

FIG. 14 is a schematic diagram showing an example of a standard download of time stamped geographic locations for a remote unit designated as "ComTrak Unit #9". In this example, the standard download times from the remote unit were determined to be at 9:50 A.M. and 3:50 P.M. on this particular day. Preferably, the information is displayed as a "map" with various landmarks and geographic locations identified thereon, for ease of interpretation. In the example shown, activity location 62b (home) and activity location 62e (work) are displayed with time stamped location information 98 displayed thereon. This stored information, downloaded from the remote unit is processed and stored at the central control station, and may be displayed at one of the graphics work stations 80 at the central control station. In addition, the customer may access the information via land line 94 using the customer's work station 92, at any time. The accumulated information in the form of a map may be displayed directly on the customer's work station, or printed in hard copy form.

Figure 15:
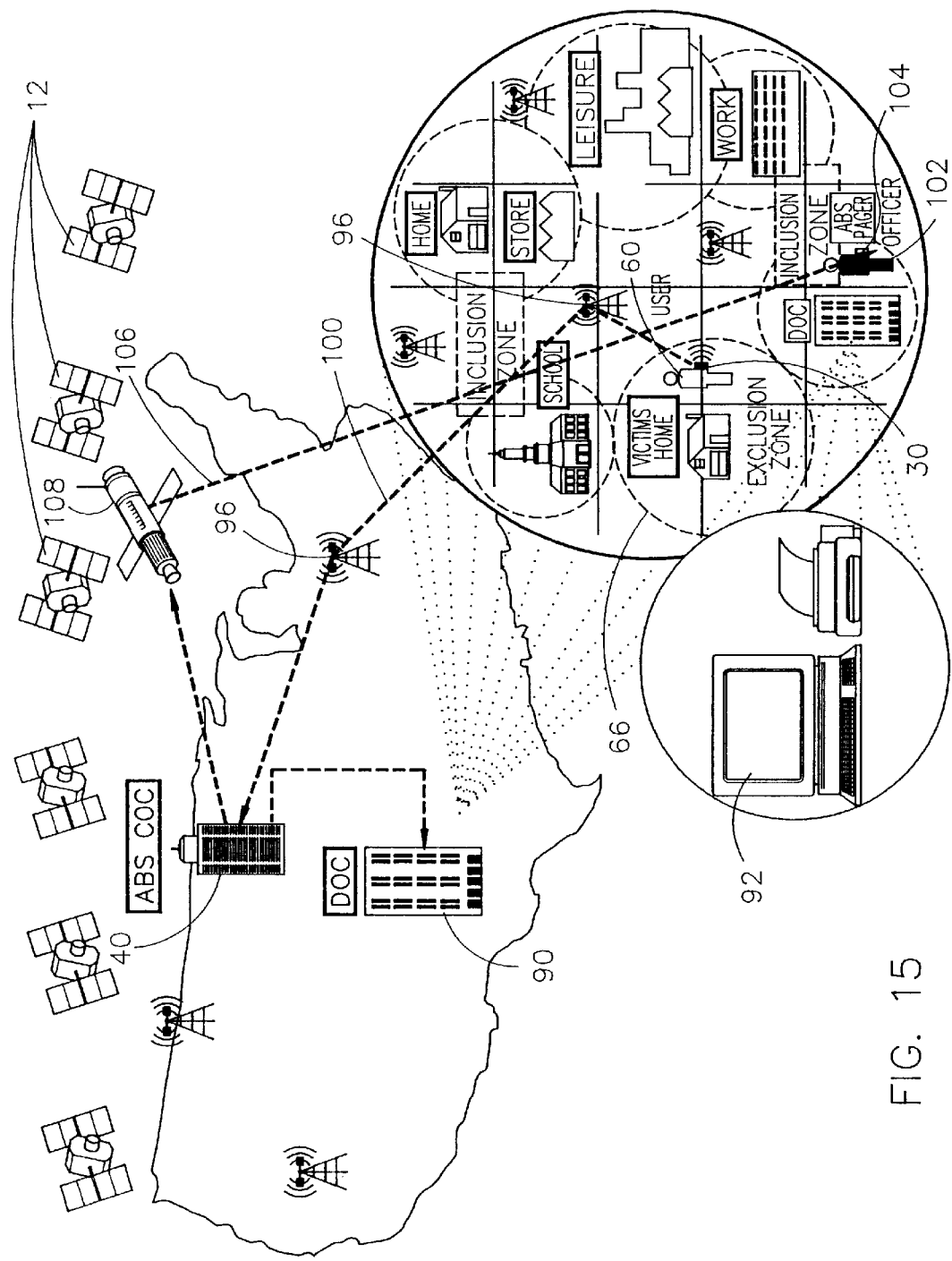
FIG. 15 is a schematic diagram showing real time notification of non-compliance with a predetermined parameter.

While the most conventional use of the system will reside in periodic standard downloads of information from a remote unit 30 to central control station 40 and thence to customer location 90, the present invention also permits "real time" notification of non-compliance with rules of compliance, and/or indicative of tampering with the remote unit 30 worn on the person of user 60. FIG. 15 is a schematic diagram showing real time notification of a non-compliance violation. In the example shown in FIG. 15, user 60 has crossed the geographic boundary into a predetermined exclusion zone 66. The CPU within remote unit 30 is continuously monitoring the user's location (via receipt of GPS signals from satellites 12 (with the current rules of compliance parameters uploaded to the remote unit 30). Upon crossing of the boundary of exclusion zone 66, remote unit 30 will immediately transmit a "violation" signal shown by arrow 100, via cellular towers 96 to central control station 40. The non-compliance violation is immediately processed at central control station 40 and transmitted to work station 92 at customer location 90, so that the customer is immediately notified of the violation. Simultaneously, the customer may provide additional instructions regarding notifications of tampering or non-compliance. In the example shown in FIG. 15, the customer has called for the central control station 40 to immediately notify a correctional officer 102 via a conventional pager 104, as shown by arrow 106 transmitted via satellite 108. The downloaded time stamped geographic location information will provide the customer and the correction's officer with the specific information necessary to correct any non-compliance or tampering violations.

Alternatively, in a medical monitoring environment, the heart rate or blood pressure of a monitored individual might be assigned certain acceptable tolerances. Clearly, these acceptable tolerances would be different for each monitored person. Thus, there is a need for an ability to store these "rules of compliance" for each monitored individual. In the preferred embodiment, this function would be performed by the remote unit 30, and periodically downloaded to the database management computer 48. The database computer 48 is in communication with controller 44 in order to receive the telephonically transmitted data from the remote units. As with the previous example, the periodically downloaded information is time stamped, to provide a doctor or other medical professional a record or "map" showing the entire accumulated record of information which was stored between the periodic standard downloads. Any occurrence of input data falling outside the acceptable compliance limits would be identified and transmitted as an alert to the graphics computer 46 for display and identification on terminals 80, and to work stations 92, as described above. In this way, the user is not required to push a "panic button", nor wait for the central control station to periodically pull the remote unit, to determine whether an emergency condition exists. Rather, a "real time" notification of an emergency condition is automatically transmitted, regardless of the scheduled time for a standard information download.

It is apparent that numerous other modifications and variations of the present invention are possible in view of the above teachings. For example, numerous environments exist for use of the present invention and each could have a particular sensor associated therewith. For example, the device could be used to monitor individuals in a radioactive or EMF environment transmitting information as to radioactivity levels or existence of poisonous gases as well as position information. Another use is by military personnel. The device can be used to track individuals such as middle crews, carrying classified information. Finally, the apparatus can be used in non-human situations such as monitoring cars.

Additionally, as is well understood in the art, many part substitutions are possible while maintaining the desired operation of the apparatus. For example, numerous CPUs are available which could accomplish the tasks equally well as those mentioned above. The same may be said for the discrete components such as microphone, temperature sensor, motion detector, etc. Similarly, a wide variety of computers are available to perform the processing and display functions in the various locations.

Finally, it will be noted that only a few of the useful environments for the present invention have been mentioned. An almost limitless number of situations can be proposed where it is desirable to monitor the position of an individual or object in conjunction with some external data.

Therefore, it is to be understood that the above description is in no way intended to limit the scope of protection of the claims and it is representative of only one of several possible embodiments of the present invention.

What is claimed is:

1. Apparatus for tracking and monitoring a remote unit from a central control station, comprising:

a remote unit having means for determining the geographic position of the remote unit at predetermined time intervals;

a programmable central processing unit (CPU) having memory storage, carried on the remote unit, and connected to the position determining means, for receiving position signals from the position determining means, for processing each position signal with a time stamp, and for storing the time stamped signals in memory;

communication means carried on the remote unit and connected to the CPU, for transmitting data from the remote unit CPU to a central control station (CCS) and for receiving data from the CCS and transmitting the received data to the CPU;

said CPU programmed to accumulate said time stamped position signals for a predetermined time interval and to transmit accumulated signals as a download through the communication means to the CCS;

said CCS located remote from the remote unit and including communication means for receiving downloads from the remote unit and for transmitting uploads to the remote unit; and said CCS including a programmable computer with memory storage, connected to the CCS communication means, for receiving, processing and storing downloads from the remote unit;

said CPU being programmable from said CCS with regard to the reception, processing and storage of information.

2. The apparatus of claim 1, wherein said computer is further programmed to process set downloads for selective display as a map with the accumulated time stamped position signals displayed on the map.

3. The apparatus of claim 2, wherein said computer includes display means for displaying a map of a selected download.

4. The apparatus of claim 3, wherein said CCS computer includes input means for enabling personnel to enter data for transmission to the remote unit CPU as an upload, said data including parameters relating to download time intervals.

5. The apparatus of claim 4, wherein said CPU is adapted to store geographic parameters constituting inclusion zones having a boundary, and is operable to compare each time stamped signal with said inclusion zone parameters, said CPU further operable to immediately transmit a "violation" signal to the CCS upon the occurrence of a time stamped signal indicating the remote unit has traveled beyond the inclusion zone boundary, said CCS computer being operable to receive and process the violation signal and to selectively display the violation on the display means.

6. The apparatus of claim 5, wherein said data for transmission to the CPU has an upload further includes geographic parameters relating to boundaries of an inclusion zone.

7. The apparatus of claim 1, wherein said CCS computer includes input means for enabling personnel to enter data for transmission to the remote unit CPU as an upload, said data including parameters relating to download time intervals.

8. The apparatus of claim 1, wherein said CPU is adapted to store geographic parameters constituting inclusion zones having a boundary, and is operable to compare each time stamped signal with said inclusion zone parameters, said CPU further operable to immediately transmit a "violation" signal to the CCS upon the occurrence of a time stamped signal indicating the remote unit has traveled beyond the inclusion zone boundary, said CCS computer being operable to receive and process the violation signal and to selectively display the violation on the display means.

9. The apparatus of claim 8, wherein said data for transmission to the CPU has an upload further includes geographic parameters relating to boundaries of an inclusion zone.

10. A method of tracking and monitoring a remote unit from a central control station, comprising the steps of:

providing a remote unit with means for determining the geographic position of the remote unit, and with a central processing unit (CPU) connected to the position determining means;

said CPU processing and time stamping position signals from the position determining means, to determine the location of the remote unit at predetermined time stamped intervals;

said CPU accumulating the time stamped position signals and storing them in memory;

said CPU transmitting a set of accumulated time stamped position signals at a predetermined time interval to a central control station (CCS);

a computer at the CCS receiving, processing, storing and selectively displaying the time stamped position signals from the remote unit;

programming said CPU from said CCS with regard to the reception, processing and storage of information.

11. The method of claim 10, wherein the step of the CCS selectively displaying the time stamped position signals includes displaying the signals as a map with each time stamp signal displayed as a position on the map.

12. The method of claim 11, further comprising the steps of:

inputting parameters in the CCS computer relating to transmission time intervals for the CPU;

transmitting the parameters to the CPU; and the CPU receiving and processing the parameters for subsequent transmissions.

13. The method of claim 12, further comprising the steps of:

inputting parameters in the CCS computer relating to geographic inclusion zones with a boundary;

transmitting the parameters to the CPU;

the CPU receiving and processing the geographic parameters; and the CPU comparing each time stamped position signal with the geographic parameters and transmitting a "violation" signal to the CCS upon the occurrence of receiving a position signal which falls outside the inclusion zone.

14. The method of claim 13, further comprising the step of the CCS computer receiving, processing and selectively displaying a "violation" signal from the CPU.

15. The method of claim 10, further comprising the steps of:

inputting parameters in the CCS computer relating to transmission time intervals for the CPU;

transmitting the parameters to the CPU; and the CPU receiving and processing the parameters for subsequent transmissions.

16. The method of claim 15, further comprising the steps of:

inputting parameters in the CCS computer relating to geographic inclusion zones with a boundary;

transmitting the parameters to the CPU;

the CPU receiving and processing the geographic parameters; and the CPU comparing each time stamped position signal with the geographic parameters and transmitting a "violation" signal to the CCS upon the occurrence of receiving a position signal which falls outside the inclusion zone.

17. The method of claim 16, further comprising the step of the CCS computer receiving, processing and selectively displaying a "violation" signal from the CPU.

18. The method of claim 10, further comprising the steps of:

inputting parameters in the CCS computer relating to geographic inclusion zones with a boundary;

transmitting the parameters to the CPU;

the CPU receiving and processing the geographic parameters; and the CPU comparing each time stamped position signal with the geographic parameters and transmitting a "violation" signal to the CCS upon the occurrence of receiving a position signal which falls outside the inclusion zone.

19. The method of claim 18, further comprising the step of the CCS computer receiving, processing and selectively displaying a "violation" signal from the CPU.

20. Apparatus for tracking and monitoring a remote unit from a central control station, comprising:

a remote unit having means for determining the geographic position of the remote unit at predetermined time intervals;

a programmable central processing unit (CPU) having memory storage, carried on the remote unit, and connected to the position determining means, for receiving position signals from the position determining means, for processing each position signal with a time stamp, and for storing the time stamped signals in memory;

communication means carried on the remote unit and connected to the CPU, for transmitting data from the remote unit CPU to a central control station (CCS) and for receiving data from the CCS and transmitting the received data to the CPU;

said CPU programmed to accumulate said time stamped position signals for a predetermined time interval and to transmit accumulated signals as a download through the communication means to the CCS;

said CCS located remote from the remote unit and including communication means for receiving downloads from the remote unit and for transmitting uploads to the remote unit;

said CCS including a programmable computer with memory storage, connected to the CCS communication means, for receiving, processing, and storing downloads from the remote unit;

said computer being further programmed to process set downloads for selective display as a map with the accumulated time stamped position signals displayed on the map, and having display means for displaying a map of a selected download;

said CCS computer including input means for enabling personnel to enter data for transmission to the remote unit CPU as an upload, said data including parameters relating to download time intervals;

said CPU being adapted to store geographic parameters constituting inclusion zones having a boundary, and being operable to compare each time stamped signal with said inclusion zone parameters, said CPU further being operable to immediately transmit a "violation" signal to the CCS upon the occurrence of a time stamped signal indicating the remote unit has traveled beyond the inclusion zone boundary, said CCS computer being operable to receive and process the violation signal and to selectively display the violation on the display means;

said data for transmission to the CPU having an upload further including geographic parameters relating to boundaries of an inclusion zone;

a computer work station at a customer location, the customer location being remote from the CCS and remote unit; and communication means connected to the customer location work station (CLWS), for transmitting data input at the CLWS to the CCS and for receiving, storing and selectively displaying data from the CCS;

said CCS communication means including means for transmitting and receiving data from the CLWS;

said CCS computer being operable to process data received from the CLWS and transmit the data to the remote unit CPU, said data including predetermined parameters;

said remote CPU being operable to process data received from the CCS relative to parameters received from the CLWS.

21. The apparatus of claim 20, further comprising:

said CCS computer being operable to transmit a "violation" signal received from the remote unit, to the CLWS; and said CLWS being operable to receive, process and selectively display a "violation" signal received from the CCS.

22. The apparatus of claim 21, wherein said means for determining the geographic position of the remote unit includes:

a receiver for receiving ranging signals from a plurality of global positioning system (GPS) satellites; and said CPU connected to the receiver and operable to process and store the GPS ranging signals and to determine the position of the remote unit therefrom.

23. The apparatus of claim 22, wherein the communication means on the remote unit includes a cellular telephone electrically connected to the CPU for transmitting and receiving information from the CCS.

24. The apparatus of claim 23, wherein the CCS computer includes a communication controller adapted to interface with a plurality of telephone lines of a telephone network and to receive telephonically transmitted information from the CPU.

25. The apparatus of claim 22, wherein said means for determining the geographic position of the remote unit further includes a receiver adapted to receive differential correction information, connected to said CPU, said CPU operable to process said GPS signals and differential correction information to determine precise location of the remote unit.

26. Apparatus for tracking and monitoring a remote unit from a central control station, comprising:

a remote unit having means for determining the geographic position of the remote unit at predetermined time intervals;

a programmable central processing unit (CPU) having memory storage, carried on the remote unit, and connected to the position determining means, for receiving position signals from the position determining means, for processing each position signal with a time stamp, and for storing the time stamped signals in memory;

communication means carried on the remote unit and connected to the CPU, for transmitting data from the remote unit CPU to a central control station (CCS) and for receiving data from the CCS and transmitting the received data to the CPU;

said CPU programmed to accumulate said time stamped position signals for a predetermined time interval and to transmit accumulated signals as a download through the communication means to the CCS;

said CCS located remote from the remote unit and including communication means for receiving downloads from the remote unit and for transmitting uploads to the remote unit;

said CCS including a programmable computer with memory storage, connected to the CCS communication means, for receiving, processing, and storing downloads from the remote unit;

said CPU being adapted to store geographic parameters constituting inclusion zones having a boundary, and being operable to compare each time stamped signal with said inclusion zone parameters, said CPU further being operable to immediately transmit a "violation" signal to the CCS upon the occurrence of a time stamped signal indicating the remote unit has traveled beyond the inclusion zone boundary, said CCS computer being operable to receive and process the violation signal and to selectively display the violation on the display means;

said data for transmission to the CPU having an upload further including geographic parameters relating to boundaries of an inclusion zone;

a computer work station at a customer location, the customer location being remote from the CCS and remote unit; and communication means connected to the customer location work station (CLWS), for transmitting data input at the CLWS to the CCS and for receiving, storing and selectively displaying data from the CCS;

said CCS communication means including means for transmitting and receiving data from the CLWS;

said CCS computer being operable to process data received from the CLWS and transmit the data to the remote unit CPU, said data including predetermine parameters;

said remote CPU being operable to process data received from the CCS relative to parameters received from the CLWS.

27. The apparatus of claim 26, further comprising:

said CCS computer being operable to transmit a "violation" signal received from the remote unit, to the CLWS; and said CLWS being operable to receive, process and selectively display a "violation" signal received from the CCS.

28. Apparatus for tracking and monitoring a remote unit from a central control station, comprising:

a remote unit having means for determining the geographic position of the remote unit at predetermined time intervals;

a programmable central processing unit (CPU) having memory storage, carried on the remote unit, and connected to the position determining means, for receiving position signals from the position determining means, for processing each position signal with a time stamp, and for storing the time stamped signals in memory;

communication means carried on the remote unit and connected to the CPU, for transmitting data from the remote unit CPU to a central control station (CCS) and for receiving data from the CCS and transmitting the received data to the CPU;

said CPU programmed to accumulate said time stamped position signals for a predetermined time interval and to transmit accumulated signals as a download through the communication means to the CCS;

said CCS located remote from the remote unit and including communication means for receiving downloads from the remote unit and for transmitting uploads to the remote unit;

said CCS including a programmable computer with memory storage, connected to thee CCS communication means, for receiving, processing, and storing downloads from the remote unit;

said computer being further programmed to process set downloads for selective display as a map with the accumulated time stamped position signals displayed on the map, and having display means for displaying a map of a selected download;

said CCS computer including input means for enabling personnel to enter data for transmission to the remote unit CPU as an upload, said data including parameters relating to download time intervals;

said CPU being adapted to store geographic parameters constituting inclusion zones having a boundary, and being operable to compare each time stamped signal with said inclusion zone parameters, said CPU further being operable to immediately transmit a "violation" signal to the CCS upon the occurrence of a time stamped signal indicating the remote unit has traveled beyond the inclusion zone boundary, said CCS computer being operable to receive and process the violation signal and to selectively display the violation on the display means;

a computer work station at a customer location, the customer location being remote from the CCS and remote unit; and communication means connected to the customer location work station (CLWS), for transmitting data input at the CLWS to the CCS and for receiving, storing and selectively displaying data from the CCS;

said CCS communication means including means for transmitting and receiving data from the CLWS;

said CCS computer being operable to process data received from the CLWS and transmit the data to the remote unit CPU, said data including predetermine parameters;

said remote CPU being operable to process data received from the CCS relative to parameters received from the CLWS.

29. The apparatus of claim 28, further comprising:

said CCS computer being operable to transmit a "violation" signal received from the remote unit, to the CLWS; and said CLWS being operable to receive, process and selectively display a "violation" signal received from the CCS.

30. Apparatus for tracking and monitoring a remote unit from a central control station, comprising:

a remote unit having means for determining the geographic position of the remote unit at predetermined time intervals;

a programmable central processing unit (CPU) having memory storage, carried on the remote unit, and connected to the position determining means, for receiving position signals from the position determining means, for processing each position signal with a time stamp, and for storing the time stamped signals in memory;

communication means carried on the remote unit and connected to the CPU, for transmitting data from the remote unit CPU to a central control station (CCS) and for receiving data from the CCS and transmitting the received data to the CPU;

said CPU programmed to accumulate said time stamped position signals for a predetermined time interval and to transmit accumulated signals as a download through the communication means to the CCS;

said CCS located remote from the remote unit and including communication means for receiving downloads from the remote unit and for transmitting uploads to the remote unit;

said CCS including a programmable computer with memory storage, connected to the CCS communication means, for receiving, processing, and storing downloads from the remote unit;

a computer work station at a customer location, the customer location being remote from the CCS and remote unit; and communication means connected to the customer location work station (CLWS), for transmitting data input at the CLWS to the CCS and for receiving, storing and selectively displaying data from the CCS;

said CCS communication means including means for transmitting and receiving data from the CLWS;

said CCS computer being operable to process data received from the CLWS and transmit the data to the remote unit CPU, said data including predetermine parameters;

said remote CPU being operable to process data received from the CCS relative to parameters received from the CLWS.

31. A method of tracking and monitoring a remote unit from a central control station, comprising the steps of:

the CPU comparing each time stamped position signal with the geographic parameters and transmitting a "violation" signal to the CCS upon the occurrence of receiving a position signal which falls outside the inclusion zone;

providing a customer location work station (CLWS) remote from the CCS;

inputting parameters into the CLWS;

transmitting the parameters to the CCS;

the CCS receiving, processing, storing and transmitting the parameters received from the CLWS, to the remote unit CPU;

the CPU receiving, processing and storing of the parameters from the CCS; and the CCS computer receiving, processing and selectively displaying a "violation signal" from the CPU.

32. The method of claim 31, further comprising the steps of:

said CCS computer transmitting a "violation" signal to the CLWS upon receipt of a "violation" signal from the CPU; and the CLWS receiving and selectively displaying a "violation" signal.

33. The method of claim 32, wherein the step of providing position determining means includes providing the remote unit with a receiver for receiving ranging signals from a plurality of GPS satellites.

34. The method of claim 33, wherein the step of transmitting accumulated signals from the CPU includes transmitting the signals over a cellular telephone to a telephone network and thence to a communication controller at the CCS computer.

35. The method of claim 33, wherein the step of providing position determining means includes providing the remote unit with a receiver for receiving differential correction information signals, and includes the step of the CPU processing ranging signals from GPS satellites and correction information signals to determine the precise position of the remote unit.

36. The method of claim 32, further comprising the steps of:

said CCS computer transmitting a "violation" signal to the CLWS upon receipt of a "violation" signal from the CPU; and the CLWS receiving and selectively displaying a "violation" signal.

37. A method of tracking and monitoring a remote unit from a central control station, comprising the steps of:

providing a remote unit with means for determining the geographic position of the remote unit, and with a central processing unit (CPU) connected to the position determining means;

said CPU processing and time stamping position signals from the position determining means, to determine the location of the remote unit at predetermined time stamped intervals;

said CPU accumulating the time stamped position signals and storing them in memory;

said CPU transmitting a set of accumulated time stamped position signals at a predetermined time interval to a central control station (CCS);

a computer at the CCS receiving, processing, storing and selectively displaying the time stamped position signals from the remote unit;

inputting parameters in the CCS computer relating to transmission time intervals for the CPU;

transmitting the parameters to the CPU;

the CPU receiving and processing the parameters for subsequent transmissions;

inputting parameters in the CCS computer relating to geographic inclusion zones with a boundary;

transmitting the parameters to the CPU;

the CPU receiving and processing the geographic parameters;

the CPU comparing each time stamped position signal with the geographic parameters and transmitting a "violation" signal to the CCS upon the occurrence of receiving a position signal which falls outside the inclusion zone;

providing a customer location work station (CLWS) remote from the CCS;

inputting parameters into the CLWS;

transmitting the parameters to the CCS;

the CCS receiving, processing, storing and transmitting the parameters received from the CLWS, to the remote unit CPU; and the CPU receiving, processing and storing of the parameters from the CCS; and the CCS computer receiving, processing and selectively displaying a "violation" signal from the CPU.

38. A method of tracking and monitoring a remote unit from a central control station, comprising the steps of:

providing a remote unit with means for determining the geographic position of the remote unit, and with a central processing unit (CPU) connected to the position determining means;

said CPU processing and time stamping position signals from the position determining means, to determine the location of the remote unit at predetermined time stamped intervals;

said CPU accumulating the time stamped position signals and storing them in memory;

said CPU transmitting a set of accumulated time stamped position signals at a predetermined time interval to a central control station (CCS);

a computer at the CCS receiving, processing, storing and selectively displaying the time stamped position signals from the remote unit;

inputting parameters in the CCS computer relating to geographic inclusion zones with a boundary;

transmitting the parameters to the CPU;

the CPU receiving and processing the geographic parameters;

the CPU comparing each time stamped position signal with the geographic parameters and transmitting a "violation" signal to the CCS upon the occurrence of receiving a position signal which falls outside the inclusion zone;

providing a customer location work station (CLWS) remote from the CCS;

inputting parameters into the CLWS;

transmitting the parameters to the CCS;

the CCS receiving, processing, storing and transmitting the parameters received from the CLWS, to the remote unit CPU;

the CPU receiving, processing and storing of the parameters from the CCS; and the CCS computer receiving, processing and selectively displaying a "violation" signal from the CPU.

39. The method of claim 38, further comprising the steps of:

said CCS computer transmitting a "violation" signal to the CLWS upon receipt of a "violation" signal from the CPU; and the CLWS receiving and selectively displaying a "violation" signal.

40. A method of tracking and monitoring a remote unit from a central control station, comprising the steps of:

providing a remote unit with means for determining the geographic position of the remote unit, and with a central processing unit (CPU) connected to the position determining means;

said CPU processing and time stamping position signals from the position determining means, to determine the location of the remote unit at predetermined time stamped intervals;

said CPU accumulating the time stamped position signals and storing them in memory;

said CPU transmitting a set of accumulated time stamped position signals at a predetermined time interval to a central control station (CCS);

a computer at the CCS receiving, processing, storing and selectively displaying the time stamped position signals from the remote unit;

providing a customer location work station (CLWS) remote from the CCS;

inputting parameters into the CLWS;

transmitting the parameters to the CCS;

the CCS receiving, processing, storing and transmitting the parameters received from the CLWS, to the remote unit CPU; and the CPU receiving, processing and storing of the parameters from the CCS.

41. The method of claim 40, further comprising the steps of:

said CCS computer transmitting a "violation" signal to the CLWS upon receipt of a "violation" signal from the CPU; and the CLWS receiving and selectively displaying a "violation" signal.

* * * * *